United States Patent [19]

Lepkofker

[11] Patent Number: 5,652,570
[45] Date of Patent: Jul. 29, 1997

[54] INDIVIDUAL LOCATION SYSTEM

[76] Inventor: Robert Lepkofker, 103 Virginia Ave., Oceanside, N.Y. 11572

[21] Appl. No.: 581,020

[22] Filed: Oct. 16, 1995

Related U.S. Application Data

[63] Continuation-in-part of Ser. No. 246,149, May 19, 1994, abandoned.

[51] Int. Cl.$^6$ ................................................ G08B 23/00
[52] U.S. Cl. ...................... 340/573; 128/690; 340/407.1; 340/539; 340/574; 342/357; 342/419; 342/450; 379/38; 395/900; 455/88; 455/38.4; 455/404; 455/521
[58] Field of Search ....................... 340/573, 574, 340/539, 407.1, 825.08; 455/100, 88–90, 53.1, 54.1; 128/690, 689, 687; 342/42, 44, 350, 352, 357, 450, 451, 458; 395/900; 379/37, 38

[56] References Cited

U.S. PATENT DOCUMENTS

| | | | |
|---|---|---|---|
| 3,478,344 | 11/1969 | Schwitzgebel et al. | 340/539 X |
| 3,710,371 | 1/1973 | Whalen et al. | 340/571 |
| 3,902,478 | 9/1975 | Konopasek et al. | 128/706 |
| 3,911,899 | 10/1975 | Hattes | 128/653.1 |
| 4,086,916 | 5/1978 | Freeman et al. | 128/661.07 |
| 4,101,873 | 7/1978 | Anderson et al. | 340/539 |
| 4,343,315 | 8/1982 | O'Leary | 128/689 |
| 4,403,215 | 9/1983 | Hofmann et al. | 340/573 |
| 4,406,290 | 9/1983 | Walbeoffe-Wilson et al. | 128/689 |
| 4,566,461 | 1/1986 | Lubell et al. | 128/668 |
| 4,596,988 | 6/1986 | Wanka | 342/457 |
| 4,598,272 | 7/1986 | Cox | 340/539 |
| 4,630,613 | 12/1986 | Dennis | 128/687 |
| 4,751,642 | 6/1988 | Silva et al. | 364/413.01 |
| 4,764,757 | 8/1988 | DeMarco et al. | 340/574 |
| 4,889,131 | 12/1989 | Salem et al. | 128/671 |
| 4,891,650 | 1/1990 | Sheffer | 342/457 |
| 4,908,629 | 3/1990 | Apsell et al. | 342/457 |
| 4,918,425 | 4/1990 | Geeenberg et al. | 340/539 |
| 5,072,598 | 12/1991 | Dibrell | 62/259.3 |
| 5,218,344 | 6/1993 | Ricketts | 340/573 |
| 5,287,398 | 2/1994 | Briault | 379/38 |
| 5,307,372 | 4/1994 | Sawyer et al. | 340/573 X |
| 5,317,305 | 5/1994 | Campman | 340/573 |
| 5,319,355 | 6/1994 | Russek | 340/573 |
| 5,333,617 | 8/1994 | Hafner | 128/697 |
| 5,335,664 | 8/1994 | Nagashima | 128/696 |
| 5,355,893 | 10/1994 | Mick et al. | 128/719 |
| 5,368,224 | 11/1994 | Richardson et al. | 128/633 |

OTHER PUBLICATIONS

Tetzeli, Rick, "Cargo That Phones Home", *Fortune* Magazine, Nov. 15, 1993, page unavailable.

*Primary Examiner*—Thomas Mullen
*Attorney, Agent, or Firm*—Alfred M. Walker

[57] ABSTRACT

An interactive individual location and monitoring system includes a central monitoring system for maintaining health, location, and other data with respect to an individual. A watch unit carried by the individual receives medical and other information selected by and inputted directly from the individual. The watch unit broadcasts the medical and other information locally by radio in a region near the individual. A belt worn pod unit is worn by the individual, including a transponder for receiving the information from the watch unit. The pod unit transmits the information to the central monitoring system. The pod unit tracks the location of the individual and transmits the location to the central monitoring system. The pod unit includes a triaxial accelerometer for gathering acceleration data for transmission of the data to the central monitoring station for analysis at a later time. The central monitoring system broadcasts alerts and queries directed to the individual and the transponder pod unit receives and rebroadcasts the alerts and queries locally. The watch unit receives the alerts and queries, and the watch unit includes a vibratory annunciator which alerts the individual of an inquiry signal from the pod unit.

19 Claims, 16 Drawing Sheets

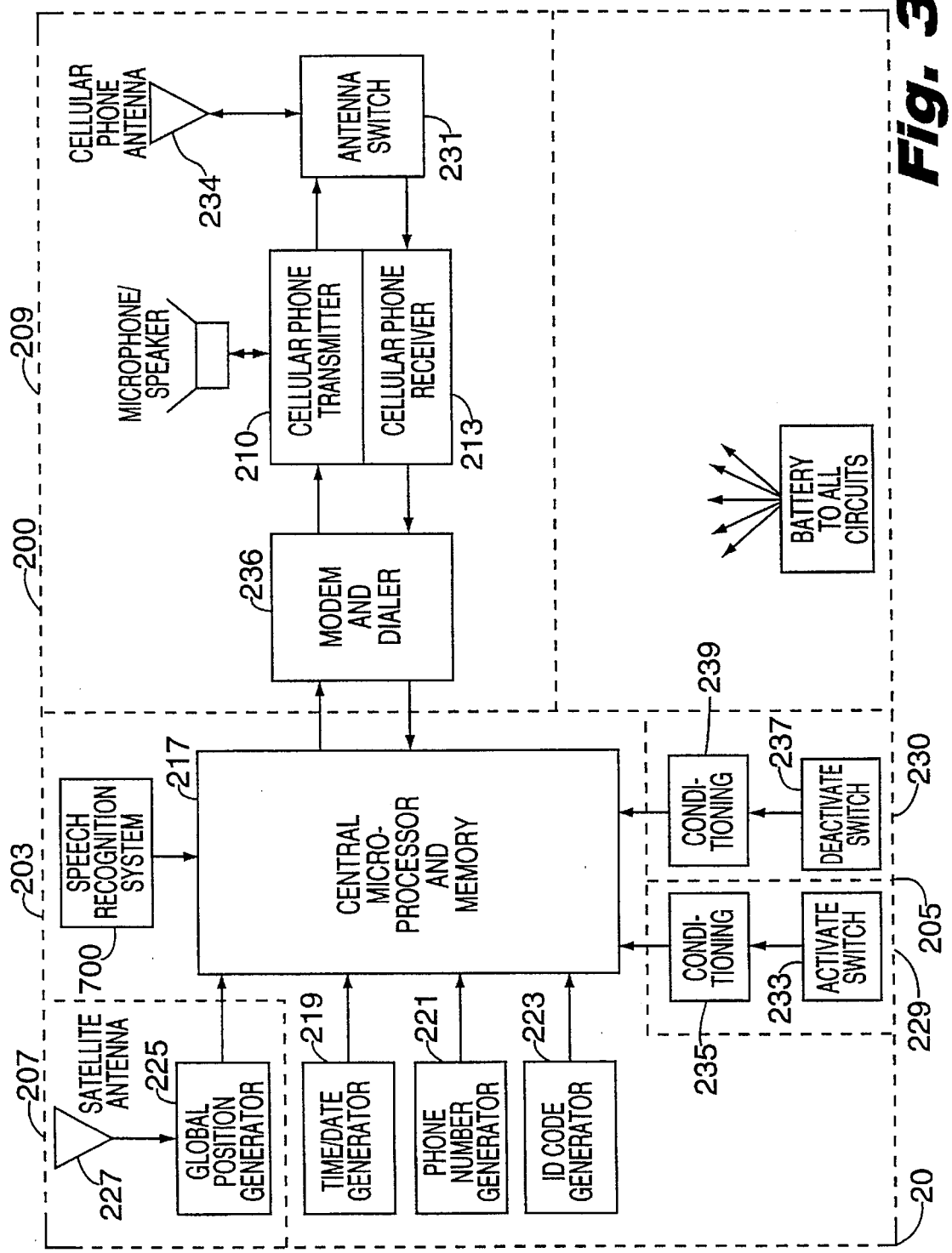

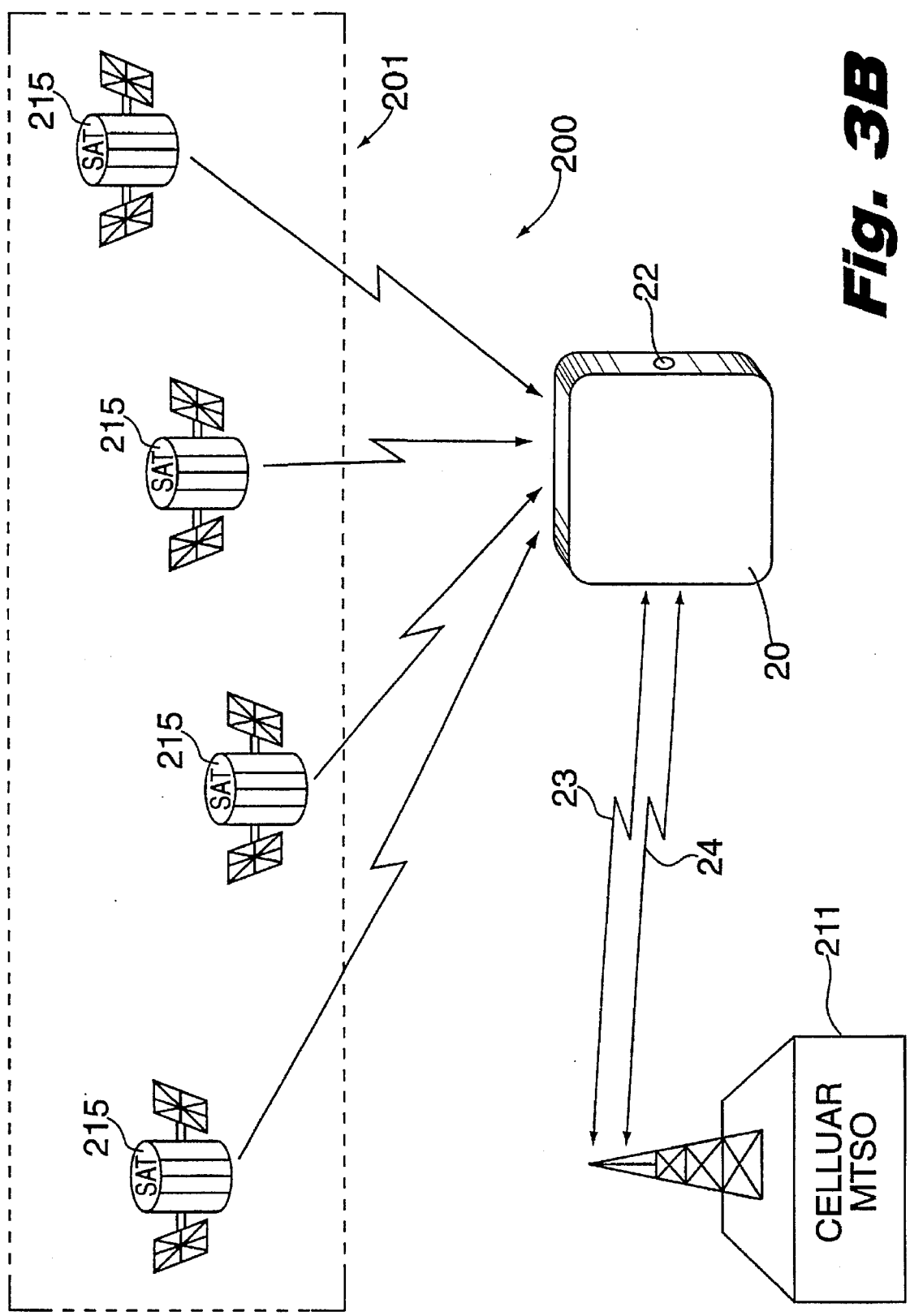

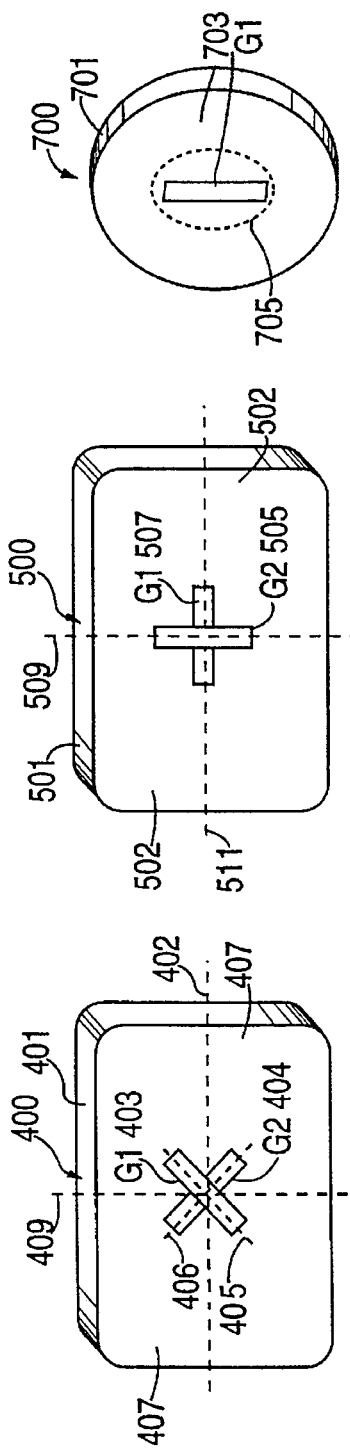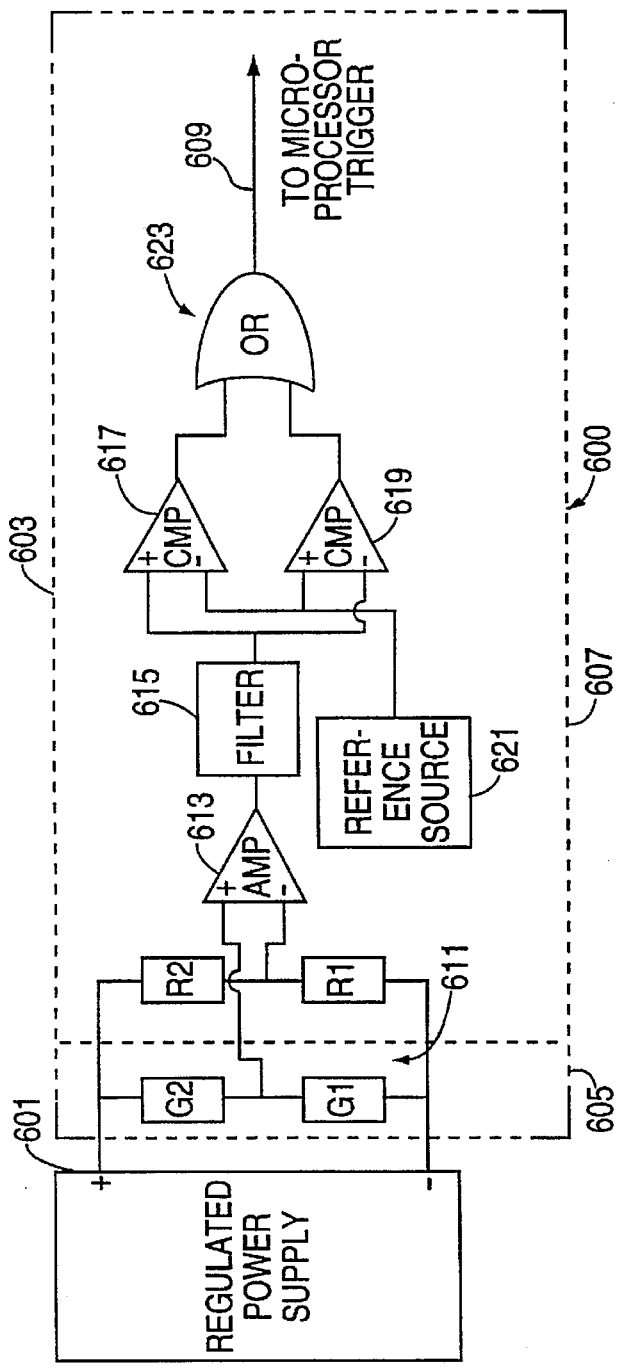

INDIVIDUAL LOCATION SYSTEM

This application is a continuation-in-part of application Ser. No. 08/246,149 filed May 19, 1994, now abandoned.

FIELD OF THE INVENTION

The individual location of the present invention preferably includes a portable two-module alarm communicator to be attached to or carried by an individual, along with a central monitoring system. Each part of the system has well-defined functions and communications protocols.

This invention also relates to a practical system for locating a selected individual carrying an object from which an alarm signal is generated. More particularly, this invention concerns a system for locating an individual carrying such an object, such as a child who is kidnaped and tracking the child's position if the child is moved. It may also locate a hiker or disabled person in a remote location, while monitoring the person's vital signs, such as pulse, heart beat or body temperature.

BACKGROUND OF THE INVENTION

There are various systems which attempt to locate a missing person by remote activation of a signal from the user at a remote location. Other devices remotely monitor the wearer of a monitoring device, to ascertain vital medical signs. However, these monitoring devices, such as portable telemetry units or wristbands, are generally confined within an institutional structure, such as in a hospital. Therefore, these medical monitoring devices are not designed for remote use outdoors, such as in a remote environmental park. Furthermore, the devices are not designed to be worn by a child or an infirm person, to track the person at a remote location of vast parameters. Moreover, existing prior art devices do not function after the transmitting portion of the device is disabled or removed from the individual using the device to provide time-line data which enable a rescuer to ascertain the whereabouts the victim by simulating where the person might be located, even without the actual functioning of the device.

The statistics on child kidnaping in the United States are significant and their effect on the child's parents and relatives is emotionally devastating.

U.S. Pat. No. 4,598,272 to Cox discloses a child monitoring device comprising two portable units, each having a radio transceiver and an antenna. One of the units, is secured to the child's person and the other is carried by the parent. The child's unit transmits a reference signal and can receive a different locator signal and has an audible alarm speaker which can be actuated by the locator signal. The parent's unit receives the reference signal from the child's transmitter and, by threshold direction, sounds a beep when the child's location exceeds a pre-determined distance. A light signal in the parent's unit remains lit as an indication that the child's unit is transmitting and that the threshold conditions have not been met. When the beep in the parent's unit indicate wandering of the child, the parent, by pressing a button, can actuate transmission of the location signal, which is stronger than the reference signal, to sound a raucous alarm in the child's unit to indicate the whereabouts of the child. Clearly this device is applicable only to very special situations and is intended to operate in a limited geographical area.

Among other prior art patents include U.S. Pat. No. 5,218,344 of Ricketts for wrist mounted transponders for surveillance of persons, such as inmates. U.S. Pat. No. 4,086,916 of Freeman, U.S. Pat. No. 4,406,290 of Walbeoff-Wilson and U.S. Pat. No. 5,335,644 of Nagashima also describe wrist watch elements in hospital settings. U.S. Pat. No. 4,918,425 of Greenberg describes a location system with speech recognition enhancers for remotely activated individual locator systems. U.S. Pat. No. 4,908,629 of Apsell and U.S. Pat. No. 4,764,757 of DeMarco also describe individual locator systems with remote activators.

Moreover, accelerometers are used in package shipping, so that if a package with sensitive equipment is dropped or damaged, the accelerometer will send a one time fixed threshold radio signal when the package is damaged. However, accelerometers are not used continuously to take a specific sample of continuous data and are not used to then include the sample of data in a data packet for a short period of time, such as five or ten seconds, and then transmit the coherent data for analysis for a predetermined period of time, such as every fifteen minutes.

Therefore, the prior art patents do not describe a novel method for transmitting data to be collected and analyzed at a later time, wherein further, the data collected is periodically updated and overridden, so that only the most recent data is processed.

Furthermore, the prior art does not disclose a system which provides a "write-only file" which provides a time-line of coherent data, as opposed to summary data, which coherent data covers, a long term period, which can be analyzed to locate a person even if the wrist watch or belt pod is detached, inactivated or damaged.

In addition, the prior art does not infer modes of transportation activities of a user, such as on foot or in a vehicle, so that the whereabouts of a missing person, such as a hiker can be rapidly analyzed and determined.

OBJECTS OF THE INVENTION

It is therefore an object of the present invention to provide an individual location system which can be used to locate a person even if the personal transmitter worn by the person is de-activated or removed from the user.

Another object of this invention is to provide an apparatus to be worn by an individual that communicates on a periodic basis with a base receiving station.

A further object is to permit the user to signal a variety of emergency situations.

It is yet another object to permit a base receiving station to solicit input from the user or his apparatus.

A further object is to monitor the user's pulse rate to initiate an emergency signal when the pulse rate is out of bounds.

Another object is to monitor and record missing pulses for transmission to a base receiving station.

It is yet a further object to permit the recording and transmission of ambient sound segments in coherent data packets which can be analyzed to simulate the approximate location of an individual, even if the user-worn apparatus is damaged or removed.

It is yet another object to record and transmit signals from a triaxial accelerometer to transmit data to a central monitoring station for analysis at a later time.

It is yet another object to simulate location coordinates of a missing person, even if the data transmitter apparatus is damaged or removed from the user.

It is a further object to monitor and analyze sounds for detection of a key word for creation of a emergency signal.

Another object is to record a time sequence of received signals at a base receiving station.

It is yet another object to analyze accelerometer data of a remote user in a time sequence to determine the type of motion activity of the user.

It is a further object to display time sequence information in a coherent fashion on a computer display at a base monitoring station for monitoring the location of individuals.

It is another object to display time sequence information overlaid on a map at a base monitoring station.

It is also an object of this invention to provide a person location system which can utilize the presently existing national cellular radio network, LORAN® transmitters, a Global Positioning System, and the Lo-Jack® system.

Another object of the present invention is to provide a child location system, which after activation, automatically locates or tracks the position of the child, which system can utilize the presently existing location systems.

A further object of the present invention is to provide a system for determining the location of an individual carrying an object, which system is believed to be practical and is able to be manufactured at a relative modest cost and which is essentially based on presently existing, or soon to be developed miniature electronic hardware.

SUMMARY OF THE INVENTION

The foregoing and related objects are obtained in accordance with the invention which, in a preferred, broad, aspect, provides a system for determining the location of an individual, comprising a remote position locating means, an object carried by the individual from which an alarm signal is generated, a remote receiver means and a remote actuation means. The remote position locating means transmits location signals in response to an interrogation signal. The object is carried by the individual and from which an alarm signal, including said location signals, are generated. The object may comprise a housing means, an alarm generating means, a pressure sensitive means, a position generating means, a transmitter and a triggering receiver means.

Preferably, the data is gathered in packets of data, so that the data can be collected and analyzed at a later time, to simulate the location of an individual, even if the position generating means and transmitter are inactivated, removed or damaged.

The alarm generation means may be disposed within the housing means and may generate an alarm signal in response to a triggering signal. A pressure sensitive means may be disposed on or within the housing means to generate a triggering signal when actuated by pressure exerted against the pressure sensitive means by the individual. The position generating means is disposed within the housing means and is coupled to the alarm generating means, for transmitting the interrogation signal to the remote position locating means and for detecting the transmitted location signal from the remote position locating means.

The transmitter means may be coupled to the alarm generating means and may be disposed within the housing means, and may transmit the alarm signal. The remote receiver means detects the alarm signal, including the location signal. The remote activation means transmits an activation signal. The triggering receiver means is disposed within the housing means and is coupled to the alarm generating means for detecting the activation signal and produces a triggering signal in response thereto.

Preferably, the present invention includes an embodiment which also monitors vital signs of a user.

In the preferred embodiment, the interactive individual location and monitoring system includes a central monitoring system for maintaining health, location, and other data with respect to the individual user, such as a hiker, infirmed person or a child.

A wrist watch means is carried by the individual user in a manner for conveniently receiving medical and other information selected by, and inputted directly, from the individual user. The information is broadcast locally by radio in a region proximate to the individual user. Preferably, a separate pod means is worn by the individual user. The pod means includes a transponder means for receiving the information from the watch means and for transmitting the information to the central monitoring system. The pod means includes a means for tracking the location of the individual user and transmits the location to the central monitoring system. In case the watch or pod means is disabled or intentionally removed, the individual user's earlier information is used to simulate the person's present location. To accomplish this simulation feature, the pod means includes a triaxial accelerometer which gathers acceleration data for transmission of the data to the central monitoring station for analysis at a later time. The central monitoring system includes a means for broadcasting alerts and queries directed to the individual user, wherein the transponder pod means receives and rebroadcasts the alerts and queries locally. The watch means includes a means to receive the alerts and queries, and a vibratory annunciator for alerting the individual to receipt of a signal from the pod means.

The watch means of the interactive individual location and monitoring system has the appearance of a wrist watch worn by the individual user in a manner to permit convenient access to input and receive information, and includes preferably only sufficient battery power to communicate without a cord to the pod means.

The pod means is secreted within the clothing of or packs carried by the individual user and carries sufficient battery power to provide long distance radio communications with the central monitoring station and to obtain location information from satellites, wherein the communications between said central monitoring system and the pod means are encrypted.

The central monitoring system includes a means for tracking and displaying the movements of the individual user.

The wrist watch includes a plurality of color coded buttons for initiating transmittal of signals representing different types of emergencies including "accident", "medical", "hold-up", and "kidnaping".

Moreover, the pod means includes alarm button means for initiating an alarm signal to the central monitoring station.

Preferably, the wrist watch includes a means for monitoring the pulse rate of the individual user and for initiating automatically the transmittal of a signal in the event a predetermined anomaly in the pulse rate indicating a medical emergency occurs.

To simulate the location of the individual user, even if the wrist watch and/or the pod is disabled, the central monitoring system further includes a write only file storage means storing periodic data packets from each client. The periodic data packets are stored in a storage means, and the periodic data packets are intermittently read only upon the occurrence of a predetermined selective event upon authorization from designated officials of the central monitoring system.

The write only file storage means provides a time line of coherent data covering a long term period, wherein subsequent periodic packets of data overlay the oldest periodic packets of data in said write only file storage means.

The triaxial accelerometer provides data to a neural network and fuzzy logic processor to infer modes of transportation activity.

The central monitoring system has a display means displaying the data, and the data display format includes alphanumeric characters and/or a graphical map format, and the data may be audio-enhanced. The graphical map data may be a multi-color graphical map display showing a global view of movement of the individual user over an extended period of time, so that the location of the user can be simulated, even if the transmitter is disabled or removed.

The present invention also includes a method of remotely and interactively communicating with and monitoring the location and condition of an individual user by establishing a central monitoring system for maintaining health, location, and other data with respect to the individual, transmitting the location and condition information from the individual to the central monitoring system by the steps of inputting information to the watch means worn by the individual, broadcasting locally by radio the information by the watch means to pod means situated among the possessions of the individual, and rebroadcasting the information by the pod means to the central monitoring systems. The central monitoring system broadcasts alerts and queries for receipt and rebroadcast by the pod means to the watch means, and the watch means alerts the individual to the receipt of the alerts and queries.

A microprocessor supports a continuous polling sequence, and monitors all alarm conditions including code word decodes and the pulse rate anomalies, remote said queries and, accumulates the data including transducer data for transmission and sending the data as a single multi-data packet to the central monitoring station.

While prior art relates to several of the elements of the present invention, the use of a triaxial accelerometer as a transducer in a personal alarm is novel. Also, the processing of the data at the central monitoring station has novel features which have not been taught by the prior art.

Although U.S. Pat. No. 5,218,344 of Ricketts teaches the use of wrist mounted transponders for surveillance of individuals and for emergency alarm communications, U.S. Pat. No. 4,086,916 of Freeman, U.S. Pat. No. 4,406,290 of Walbeoff-Wilson and U.S. Pat. No. 5,335,664 of Nagashima all teach the use of wristwatch elements as pulse rate monitors or as parts of cardiac monitoring systems, and, while the present invention also uses a wrist watch element, which has a pulse monitoring subsystem and at least one alarm button, it is the processing of the information which differs.

The speech recognition means of Greenberg, U.S. Pat. No. 4,918,425 is related to that feature in the wrist watch portion of the present invention. However, in the present invention, the wrist watch unit has a microprocessor which supports a continuous polling sequence monitoring the alarm buttons, commands from the belt pod unit, code word decoding, and pulse rate out of bounds. Data for transmission to the pod unit is accumulated and sent as a single, multi-data transmit packet. Requests for activation of the vibratory annunciator in the wrist watch are also handled.

While DeMarco, U.S. Pat. No. 4,764,757, Apsell, U.S. Pat. No. 4,908,629 and Greenberg, U.S. Pat. No. 4,918,425 teach the use of remote activation and satellite communications in tracking people carrying transponders, they are totally involved with "real-time" situation handling. The present invention also does this in response to a variety of alarm stimuli.

In addition, the concept of the "write only file" distinguishes the present invention from the cited prior art. The intent here is to provide a time-line of coherent data (as opposed to summary data) covering a long term period (such as 24 hours or more).

This data is of use for intense analysis regardless of the present functional condition of the remote user equipment, such as the wrist watch or belt pod units. The latter can be easily detached, destroyed, or removed from the individual (consider water damage in a drowning situation for example).

The analysis of the triaxial accelerometer data via neural network and fuzzy logic to infer modes of transportation activity provides information which has not been available from previous systems.

The presentation of the data starting from sensitivity to the privacy issue to the two modes of display also has not been demonstrated in the cited prior art. For example, the time line display is an audio-enhanced time-coherent detailed alphanumeric display. The multi-color graphical map display is a global view of subject movement over an extended period. By using the two modes of display together, the data from the w.o. file can support law enforcement or rescue agencies in rapid analysis of long term data. Biological data, such as pulse rate and missing pulses is used in context in understanding the movements of a subject from one location to another using a variety of conveyances with live snapshots of ambient sounds.

DESCRIPTION OF DRAWINGS

The invention is illustrated in the drawings in which like reference numerals designate the same or similar parts throughout the figures of which:

FIGS. 3A and 3B are simplified block diagrams of the geoposition cellular system for determining the location of an individual;

FIG. 5A depicts a simplified perspective view of a key fob with its interior strain gage elements shown in solid lines;

FIG. 5B depict a simplified perspective view of a key fob with another embodiment of its interior strain gage elements shown in solid lines;

FIG. 5C depict, a simplified perspective view of a pendant with its strain gage elements shown in solid lines; and FIG. 5D is a schematic diagram of the pressure sensitive means circuit utilized in all three systems;

DETAILED DESCRIPTION OF THE DRAWINGS

The preferred embodiment for an individual location system as depicted in FIGS. 7–11 includes a wrist watch device WW, a belt pod device BP and a central monitoring system CMS. All three subsystems WW, BP and CMS communicate to each other by radio transponders. The protocols and radio frequencies RF are optimized for the particular functions.

For example, the communications of the wrist watch WW and the belt pod BP device can be handled by a very low power RF link from VLF through microwave frequencies as the distance to be covered is just a few feet.

The belt pod unit BP can be disguised as a "beeper" attached to a belt, or belt pod unit BP can just as easily be a unit carried in a purse or built into a large pendant.

Each frequency band has pros and cons for this application. For example, VLF has a tendency to follow the surface of the body of the individual and can operate in an "induction" mode using small coils to couple to the skin instead of an actual antenna. UHF or microwave frequencies require very small antenna elements but tend to be more expensive and directional.

The remote RF link between the belt pod unit BP and the central monitoring system CMS can be a standard analog or digital cellular telephone link or a two-way messaging system such as a Personal Data Network (PDN). The locator system as described in FIGS. 7–11 uses a communications infrastructure that is already in place and very widely distributed. To prevent tampering, all communications between belt pod unit BP and central monitoring system CMS are encrypted.

Figure 7:
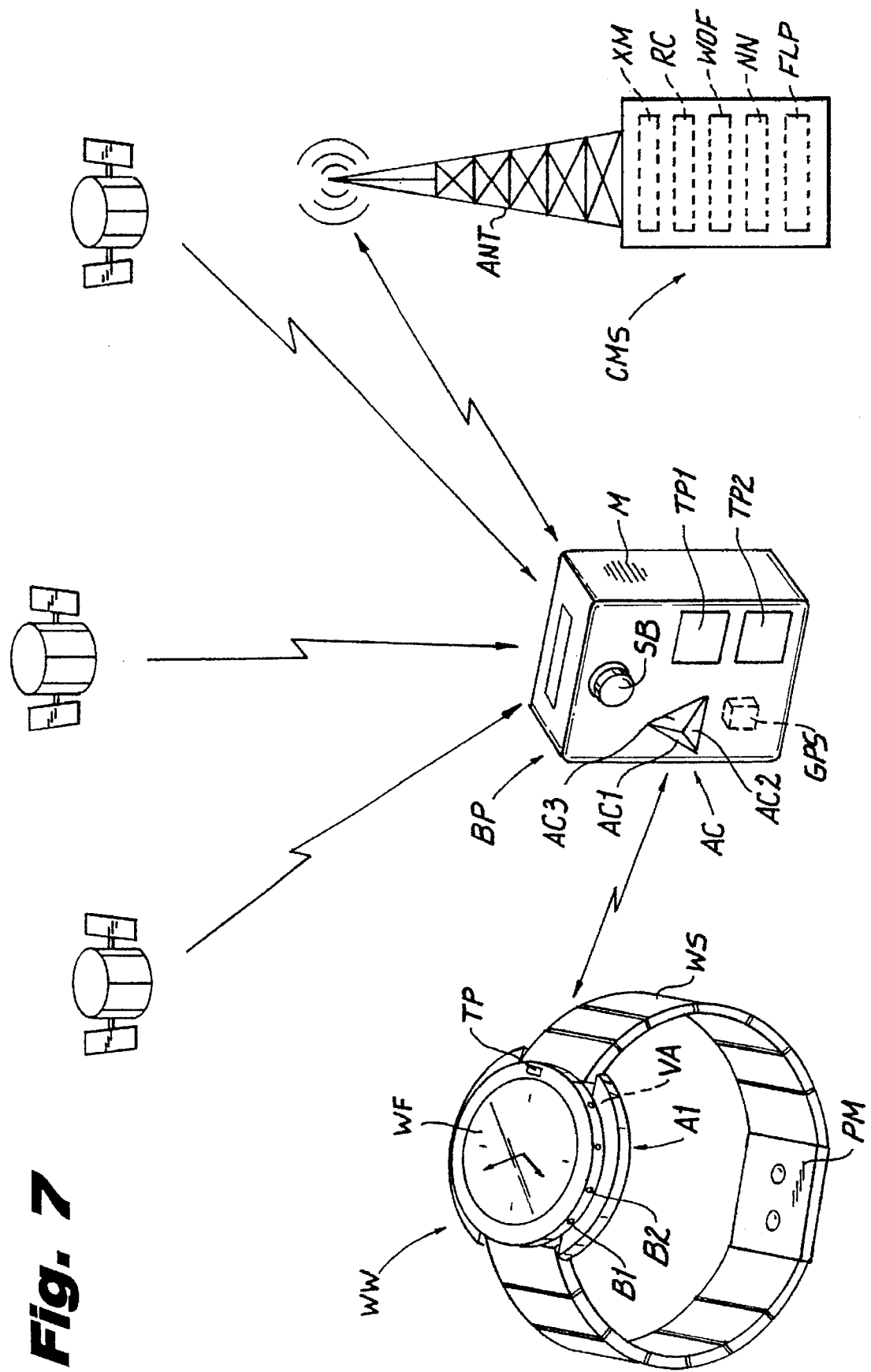
FIG. 7 is a system diagram of the components of another embodiment for a individual locator system of the present invention.

As shown in FIG. 7, central monitoring system CMS uses antenna ANT, receiver RC and transmitter XM to communicate with belt pod BP via its transponder TP2. Transmitter XM is used to broadcast alerts and queries to the various client belt pod BP units. Additional elements of the central monitoring system to be discussed are the write only file WOF which is implemented as part of the central computer memory, the neutral network NN and the fuzzy logic processor FLP.

Wrist watch unit WW includes a standard functional watch face WF to disguise the alarm unit A1. In addition, watch unit WW has multiple buttons B1, B2, etc. which can be distinguished by color. These permit the user to call the central monitoring system CMS via the belt pod unit BP and indicate different types of emergencies such as "accident", "medical", "hold-up", or "kidnaping" for example.

In addition, the watch strap WS has a pulse monitor PM of a well known infrared type along with a missing pulse detector for monitoring irregular heartbeats. Wrist watch unit WW may include a silent vibratory annunciator VA similar to features on some beepers, to indicate to the wearer that the central monitoring system (CMS) is requesting some response, wherein the vibratory annunciator VA is more discreet than a buzzer.

A microphone to support a speech analyzer function for keyword signaling may be also included in the wrist unit WW. Since space is at a premium in this unit, energy conservation is paramount to feasible operation for long periods with little space for batteries. To facilitate this, all transmission of signals to belt pod unit BP is in short data bursts. Local storage and micro controller oversight sample and store data, then assemble messages for transmission. Receiver functions are continuous since this is a low power activity and needs to be ready to respond to inquiries from the belt pod unit BP.

Belt pod unit BP has two transponders, TP1 and TP2. TP1 communicates with wrist watch unit WW via transponder TP, which is a very local link, and TP2 communicates with central monitoring system CMS, which is a remote link. In addition, a complete GPS (Global Positioning System) navigation system GPS is included. This receives signals from at least three separate satellites to calculate the local longitude and latitude. FIG. 7 shows navigation system GPS combined with transponder TP2, both located in belt pod BP. Both navigation system GPS and transponder TP2 send location information to central monitoring system CMS which is received through antenna ANT and receiver RC to provide means for tracking an individual. Transponder TP2 in belt pod BP also receives alerts and queries broadcast by the central monitoring system CMS; using local transponder TP1 (as appropriate) to communicate with the wrist watch WW via its transponder TP, data is elicited for response to these alerts and queries from the central processing system CMS. The operation of the belt pod unit BP is also supervised by a micro controller which oversees the handling of various signals and alarms. A signal button SB to send an alarm to the central monitor system CMS is included in case wrist watch unit WW is damaged or lost. Three mutually orthogonal accelerometers AC1, AC2, AC3, or a single triaxial type, are included in belt pod unit BP. A microphone M for ambient sounds is also housed in belt pod unit BP.

Flowchart Descriptions

Figure 8A:
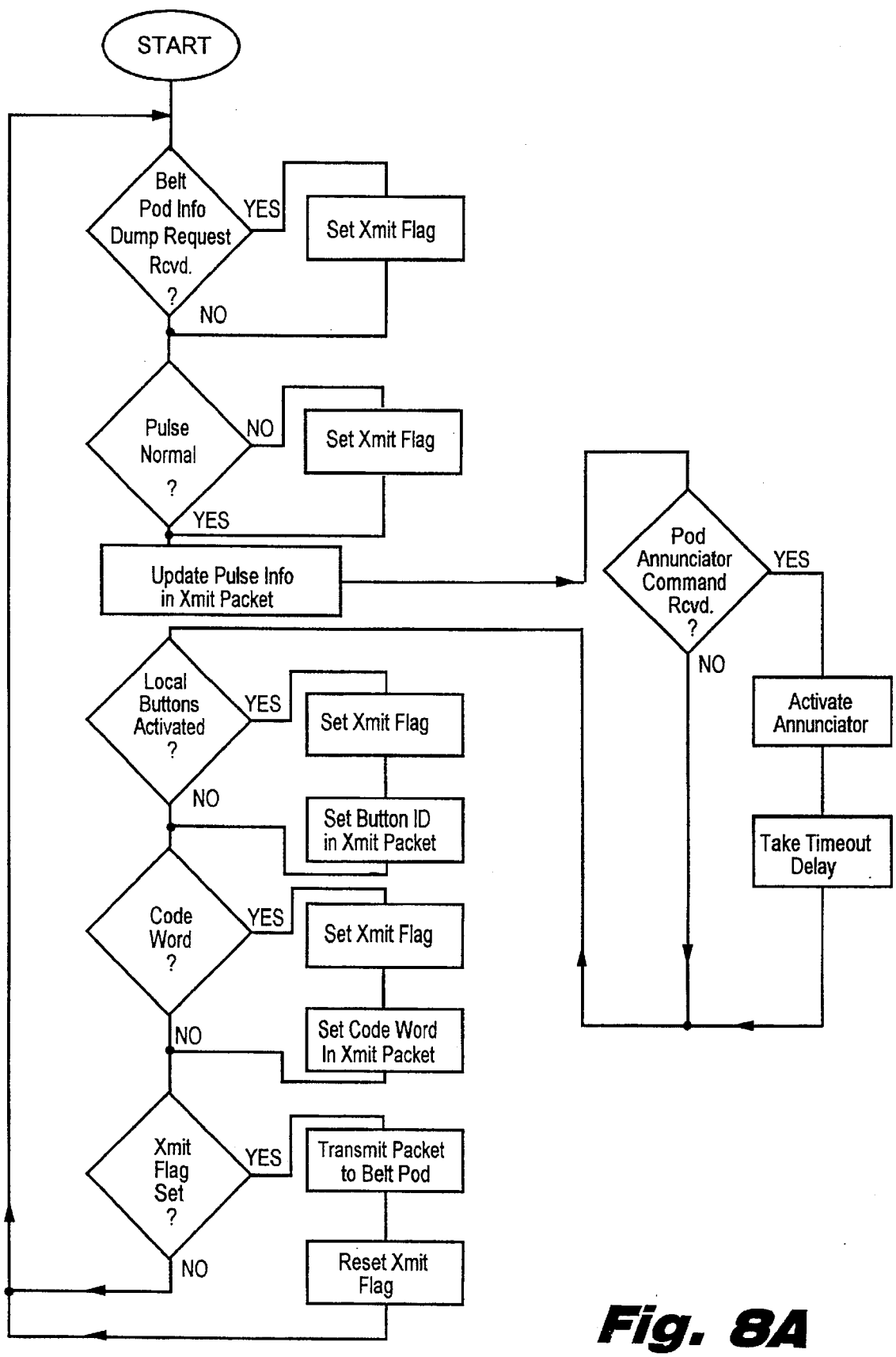
FIG. 8A is a flowchart of the wrist watch components of the embodiment as in FIG. 7.

FIG. 8A shows a flowchart of the main polling loop of the micro controller of wrist watch WW. Other operations such as analysis of pulse information or secret code word identification analysis are not detailed. These are handled by a separate digital signal processor or by the same micro controller. Belt pod unit BP routinely sends information dump requests to wrist watch WW. If one is received, the transmit flag is set. Other events which cause the transmit flag to be set are abnormal pulse, local alarm buttons, or secret code word deciphered. In most cases, some information is updated or added to the "xmit packet" which is transmitted to the belt pod unit BP.

Figure 8B:
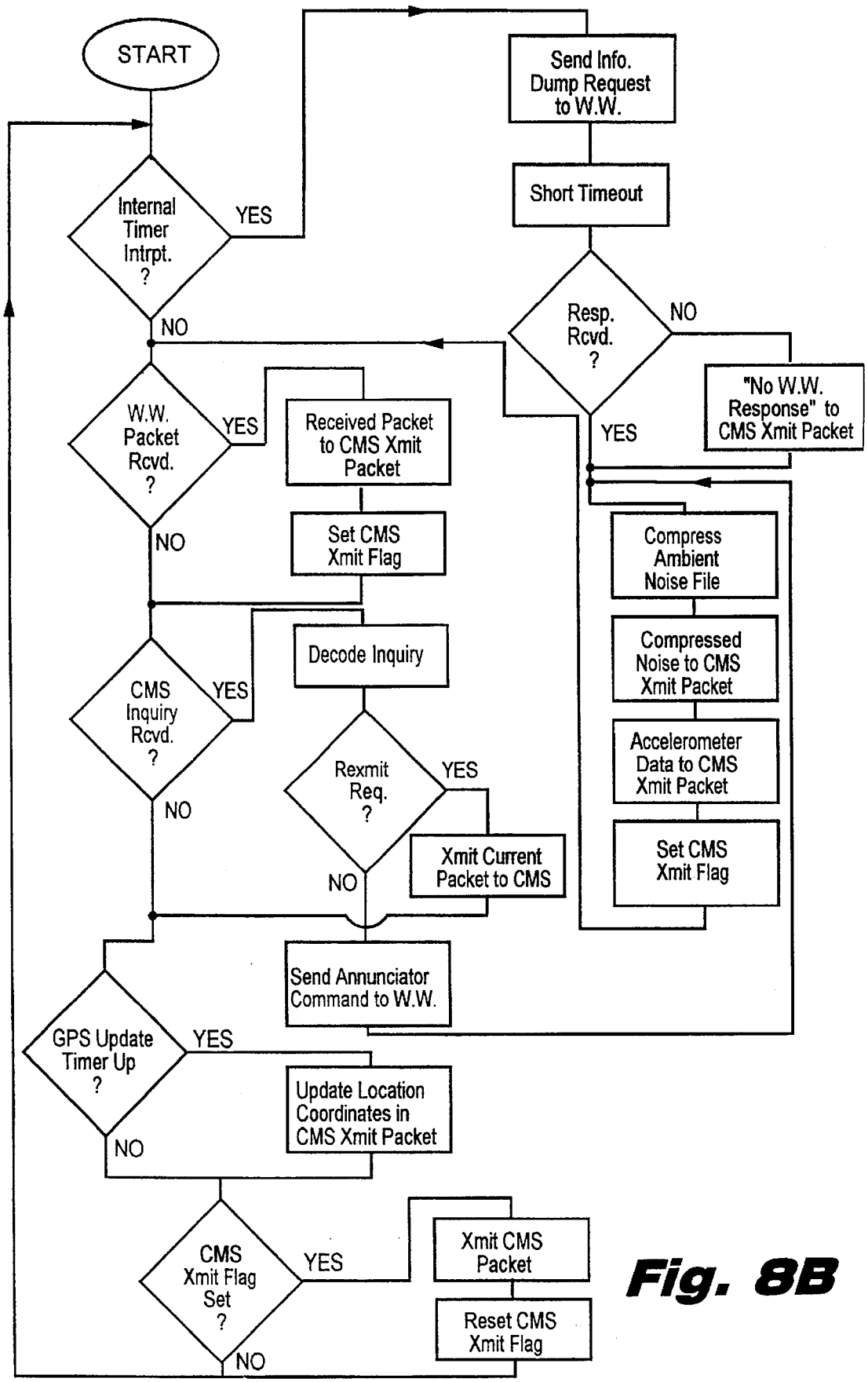
FIG. 8B is a flowchart of the belt pod of the embodiment as in FIG. 7.

FIG. 8B shows a flowchart of the main loop of the micro controller of belt pod unit BP. Belt pod unit BP communicates with wrist watch WW as well as with the central monitoring system (CMS). A similar technique to that used in the wrist watch WW is used in belt pod unit BP in transmissions to central monitoring system CMS.

Updates or additions are placed in a transmit packet to the central monitoring system CMS before the actual transmission. The first decision block asks if a timer interrupt has occurred. This may be regular or pseudorandom in nature. This interrupt triggers an information dump request to the wrist watch WW.

A short timeout is taken to wait for a response; if no response is received, this is noted in the transmit packet XMIT. No user intervention is requested. The ambient noise file continuously overlays a small memory file, such as a 5-second sound bite which is then compressed and added to the transmit packet XMIT. Similarly, accelerometer data is added to Xmit file, and the Xmit flag is set.

Next, if wrist watch WW packet has been received, this information is added to the Xmit packet to central monitoring system CMS and the flag is set. The Xmit flag may be redundantly set with no problem. If an inquiry of central monitoring station CMS has been received, the inquiry is decoded to ascertain if it is simply a retransmit request for the last inquiry. If so, the current Xmit packet to the central monitoring system CMS is retransmitted; otherwise an annunciator command is sent to wrist watch WW, which requires a user response as in the flowchart of wrist watch WW. GPS location updates are timed locally and the coordinates are updated or a non-reception note is added to the Xmit packet.

Figure 8C:
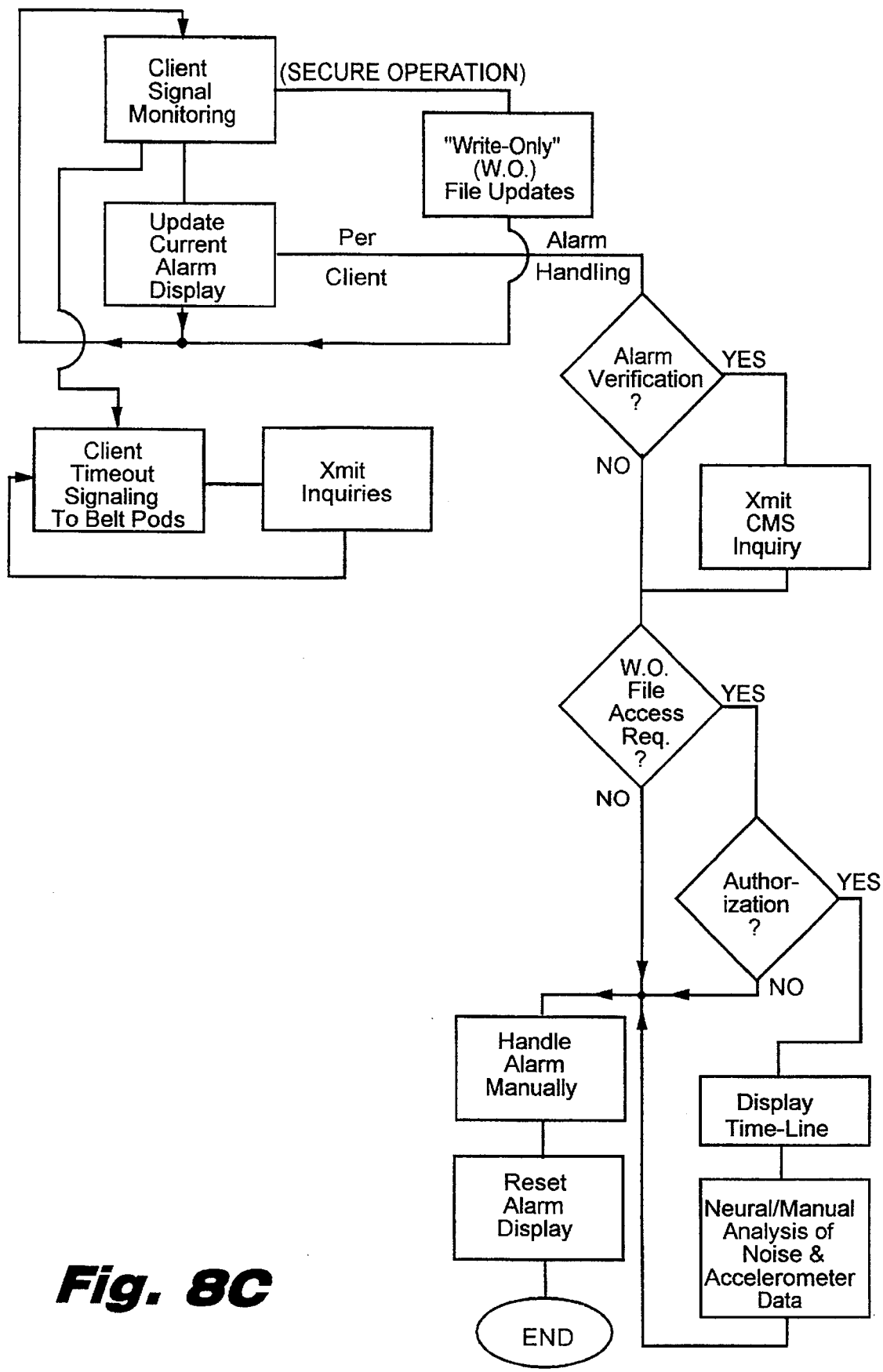
FIG. 8C is a flowchart of the central monitoring system of the embodiment as in FIG. 7.

FIG. 8C shows a central monitoring station flowchart at a macro level. Client signals are continuously monitored. Since belt pod unit BP sends periodic updates, if a timeout occurs for a specific user, an inquiry is transmitted to the user. As signals arrive, any alarm conditions are noted and immediately brought up on the current alarm display. Other actions to alert the monitoring personnel such as audible alarms or highlighting may also be used. Routine non-alarm signals are used to update a secure file for each user known as the "Write-Only" or WO file. It is called a "write only" file because in normal circumstances, the file is never read. The write only file is a fixed size file for each user and it may be as small as 30 kilobytes or as large as several megabytes.

The size of the write only file depends on the frequency of the updates from the user, the length of the continuous data samples transmitted, and whether the data is compressed, before or after it is sent.

The write only file is continuously overlaid in a prescribed sequence such that at least a 24 hour "time line" data sequence detailing pulse rates, missing pulses, sound samples (brief sound bites), accelerometer readings, and time-stamped location coordinates is maintained to help simulate the location of a user, even if either wrist watch WW or belt pod unit BP are damaged or removed.

Figure 9:
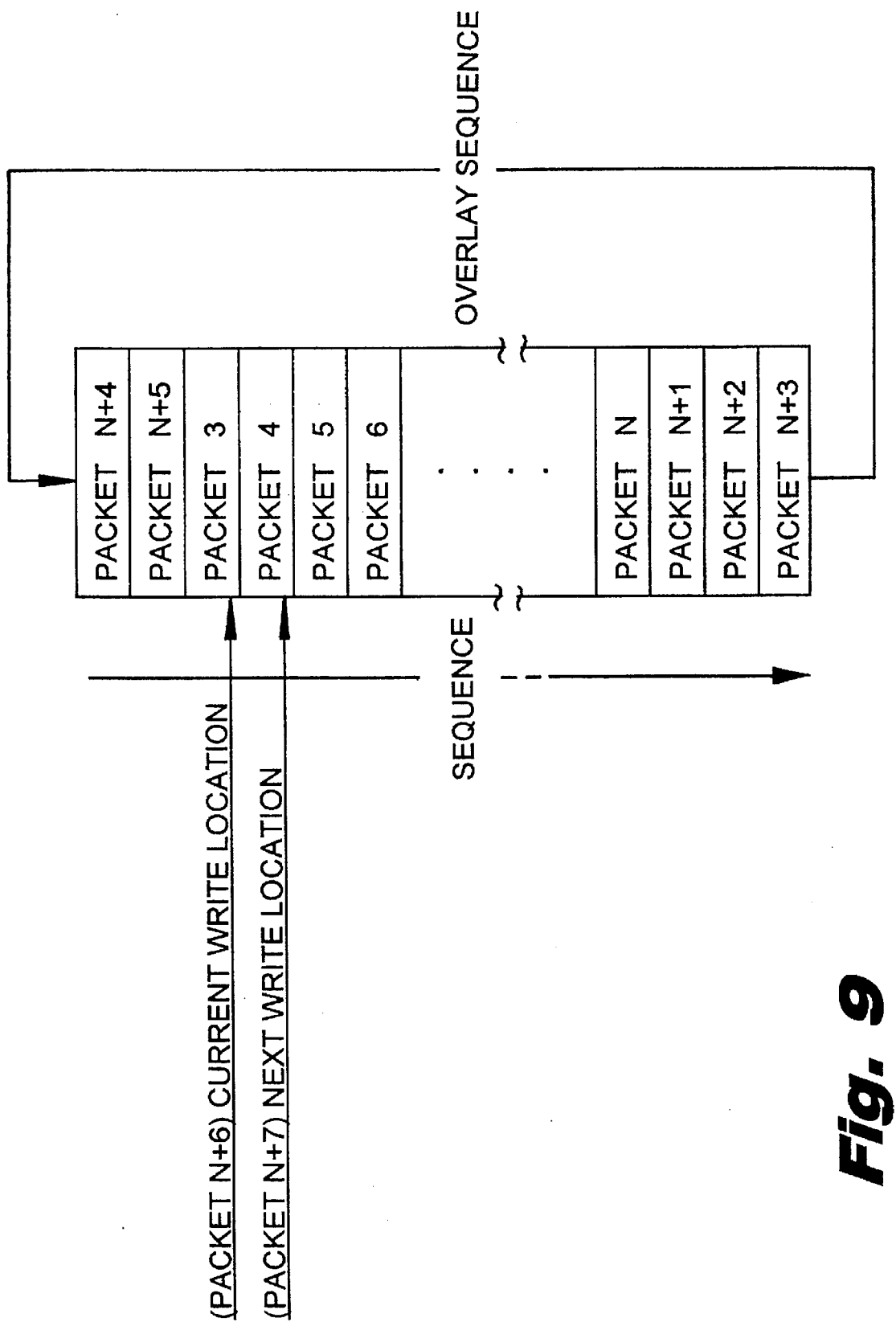
FIG. 9 is a sequential diagram of the "Write-Only" file overlay sequence of the embodiment as in FIG. 7.

FIG. 9 illustrates the overlay sequence. Since routine reading of such a file would be a serious breach of privacy, reading this file is only permitted by established authorization procedures. If properly authorized, the write only file for a user can be read to display the time line. Also, neural network analysis of accelerometer data can be used to determine if the user is walking or riding in a car, boat, small plane, airliner or train. This analysis can be overlaid on sound byte data in a time coherent manner so that investigators can piece together the recent time history of the client. This may be vital in a suspected kidnapping situation to help locate the client even if the alarm is presently inoperative or has been removed from the client.

An Endevco micro miniature triaxial piezoelectric accelerometer AC, such as their model 23 can be used in the belt pod unit BP to source the three dimensional acceleration inputs. At the base station this data, as short samples covering a few contiguous seconds, is put through a neural network that has been previously trained on live data to distinguish between walking, running, riding in a car, boat, train, bus, plane, etc. The neural network is also post processed through a fuzzy logic computer to help classify ambiguous situations such as "walking inside a moving train".

Figure 10:
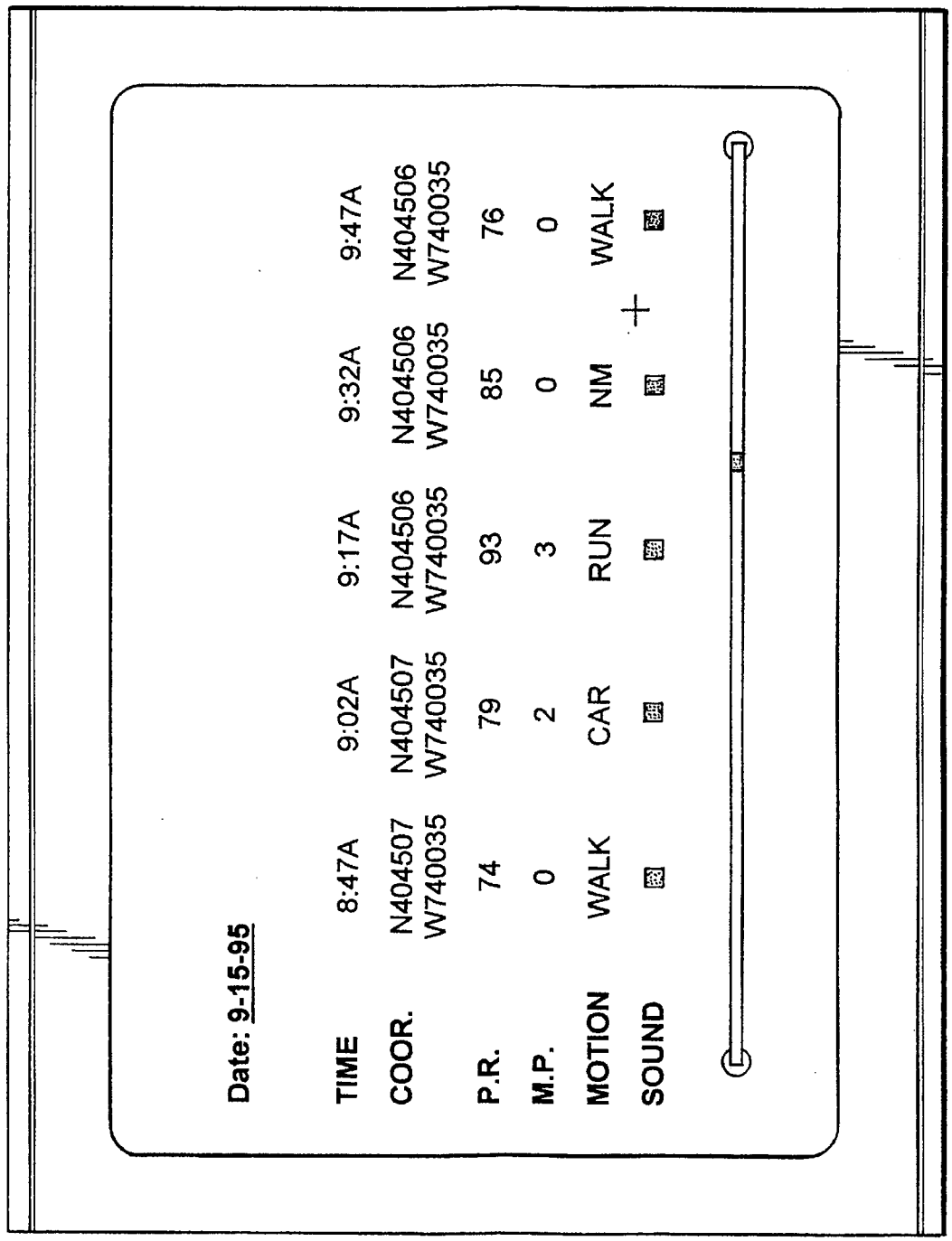
FIG. 10 is a front elevational view of a typical time line display of the embodiment as in FIG. 7, and, FIG. 11 is a front elevational view of a multi-color graphical map display of the embodiment as in FIG. 7.

FIG. 10 shows a typical time line display of a user at central monitoring system CMS. The investigator at the central monitoring system CMS can scroll through the write only file contents in time sequence by using a mouse to place the cursor on the right or left end of the scroll bar at the bottom of the screen and "clicking". The coordinate display gives the latitude and longitude as derived from the GPS data sent. Reference symbol PR denotes pulse rate and reference symbol MP denotes missing pulses. "Motion" is the determination from the neural/fuzzy analysis of the accelerometer data, wherein "NM" stands for no motion. By placing the cursor on a sound command mark and clicking, the actual sound bite is played on the speakers of the computer system.

Figure 11:
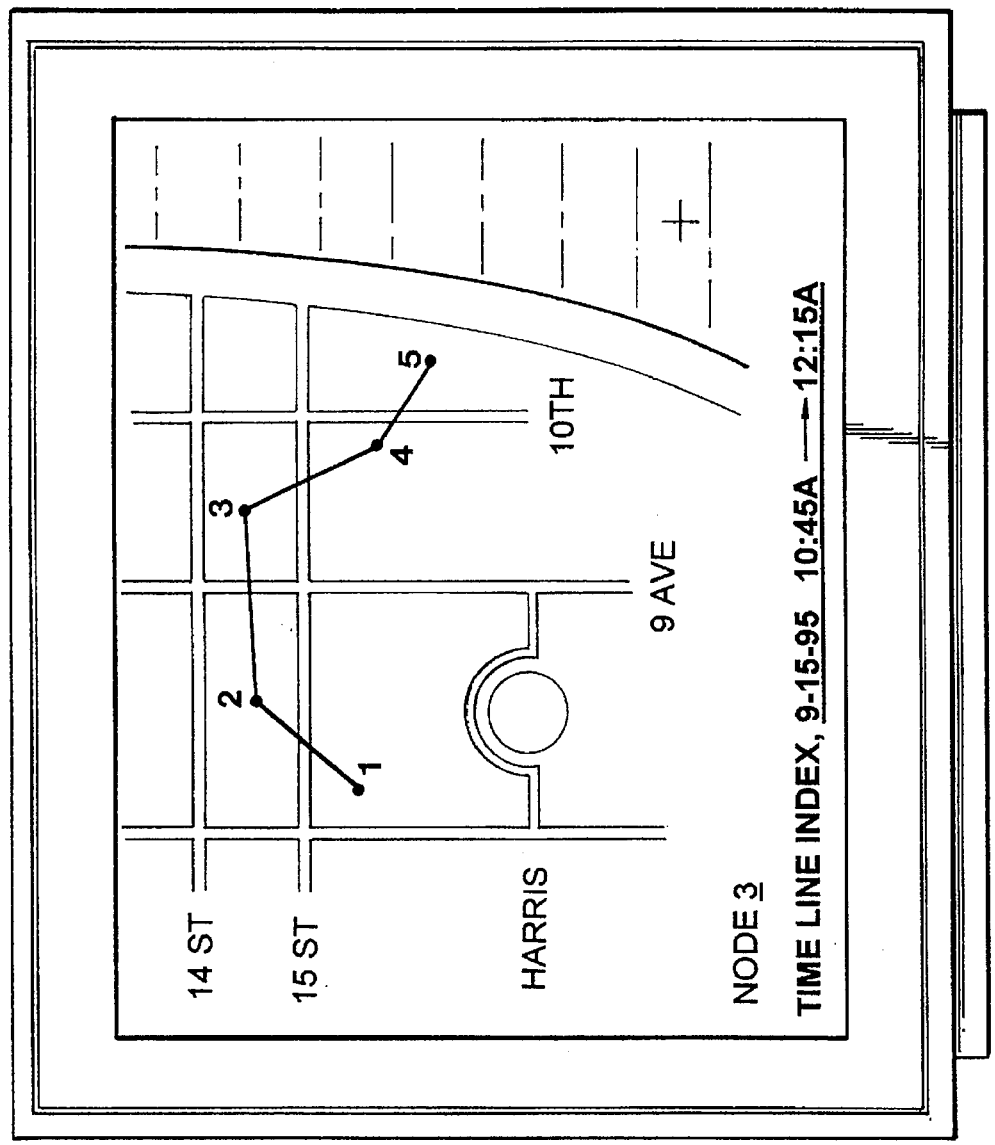

FIG. 11 shows a typical map display of a user at central monitoring system CMS. The map is stored in a map archive file at central monitoring station CMS. The proper map and scale for display is determined through analysis of all of the location coordinates in each data packet in the write only file being analyzed.

The map details are displayed in a subdued color such as red. Next, the subject path is properly overlaid on the map in time sequence with a node number at each distinctly different location in the data or at each major inflection point. By placing the cursor on a node number and clicking the mouse, the time line index information is displayed giving the time period that the subject spent at the node location or vicinity. This information can be used to index back into the time line display for further analysis, to simulate or infer the current location of the user.

In another embodiment, as shown in FIGS. 1–6, the objects carried by an individual from which an alarm signal is generated, which is part of a system for determining the location of the individual, are depicted in FIGS. 1A, 1B, 1C, 1D, and comprise a watch 1, a key fob 20, and a pendant 40; the preferred object being the key fob 20.

Figure 1A:
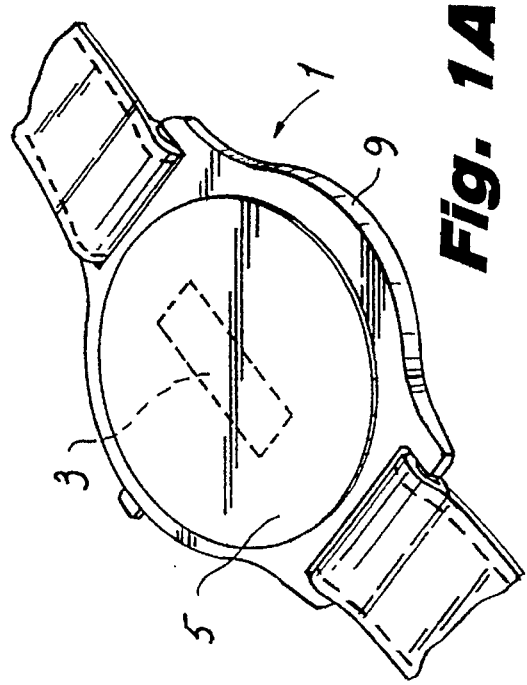
FIGS. 1A, 1B, 1C and 1D depict respectively, simplified perspectives of a watch, front and back, a key fob and attached key and a pendant with a portion of its attached chain.
Figure 1D:
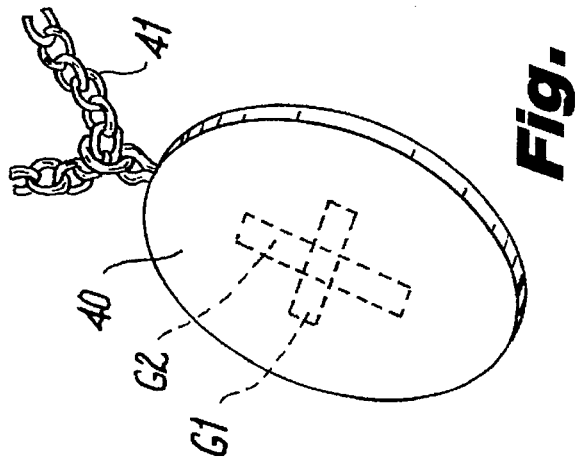
Figure 1B:
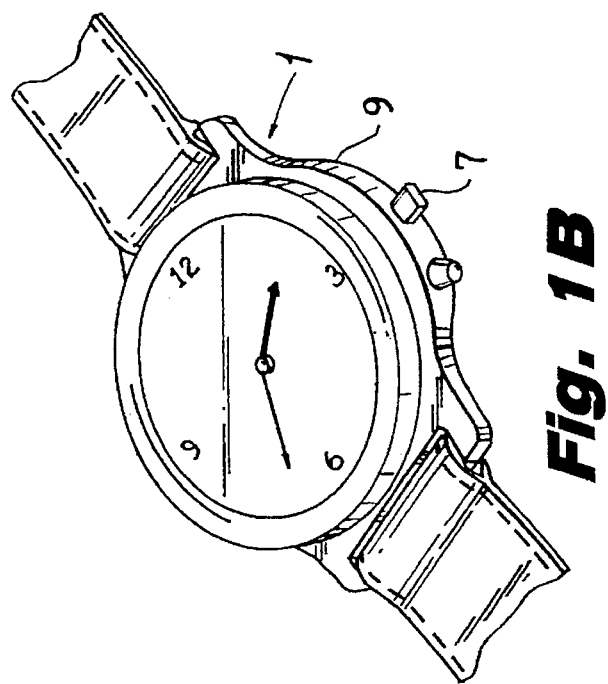
Figure 1C:
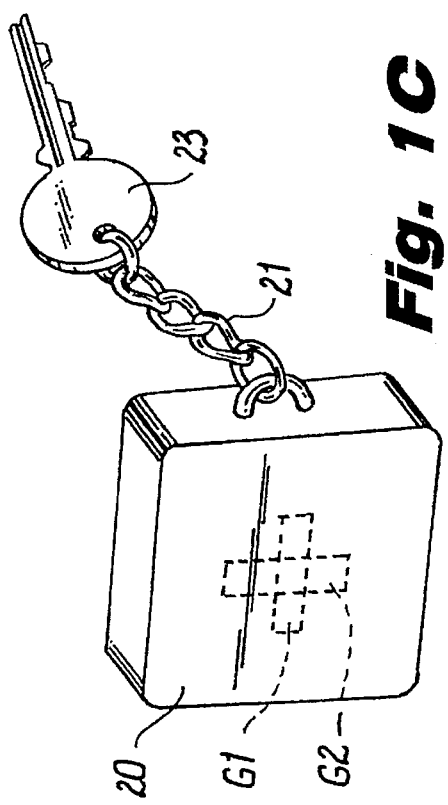

The watch 1 is usually worn around the wrist of the individual and the pressure sensitive element or elements 3, discussed in detail subsequently, are disposed inside the back cover 5 in one embodiment (FIG. 1A) and wherein the pressure sensitive element(s) 3, comprise a push button switch 7 disposed within its case 9, in another embodiment (FIG. 1B). The latter is the preferred embodiment. The pressure sensitive element(s) 3 preferably used is a strain gage, but other pressure transducer(s) can be utilized. The key fob 20 is depicted in FIG. 1C having gages G1 and G2 disposed within the housing thereof and attached to chain 21 which is connected at its end to a key 23. The pendant 40 is depicted in FIG. 1D having gages G1 and G2 disposed on its back or within its housing (not shown) and attached to a chain 41 and worn around the neck of the individual. In all these several objects, the wrist band and the chain can comprise the antenna of the system.

Figure 2A:
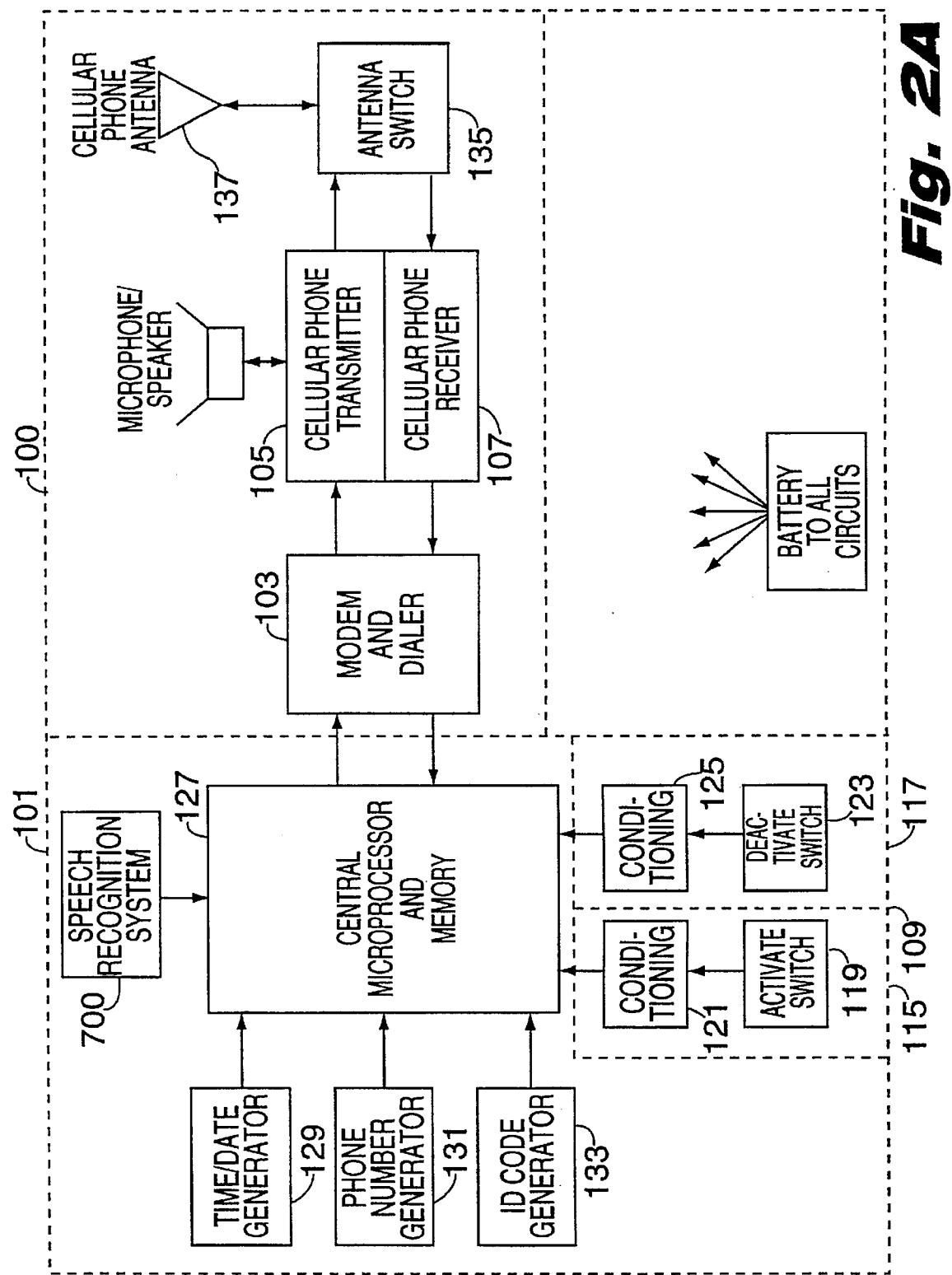
FIGS. 2A and 2B are simplified block diagrams of a cellular triangulation system for determining the location of an individual.
Figure 2B:
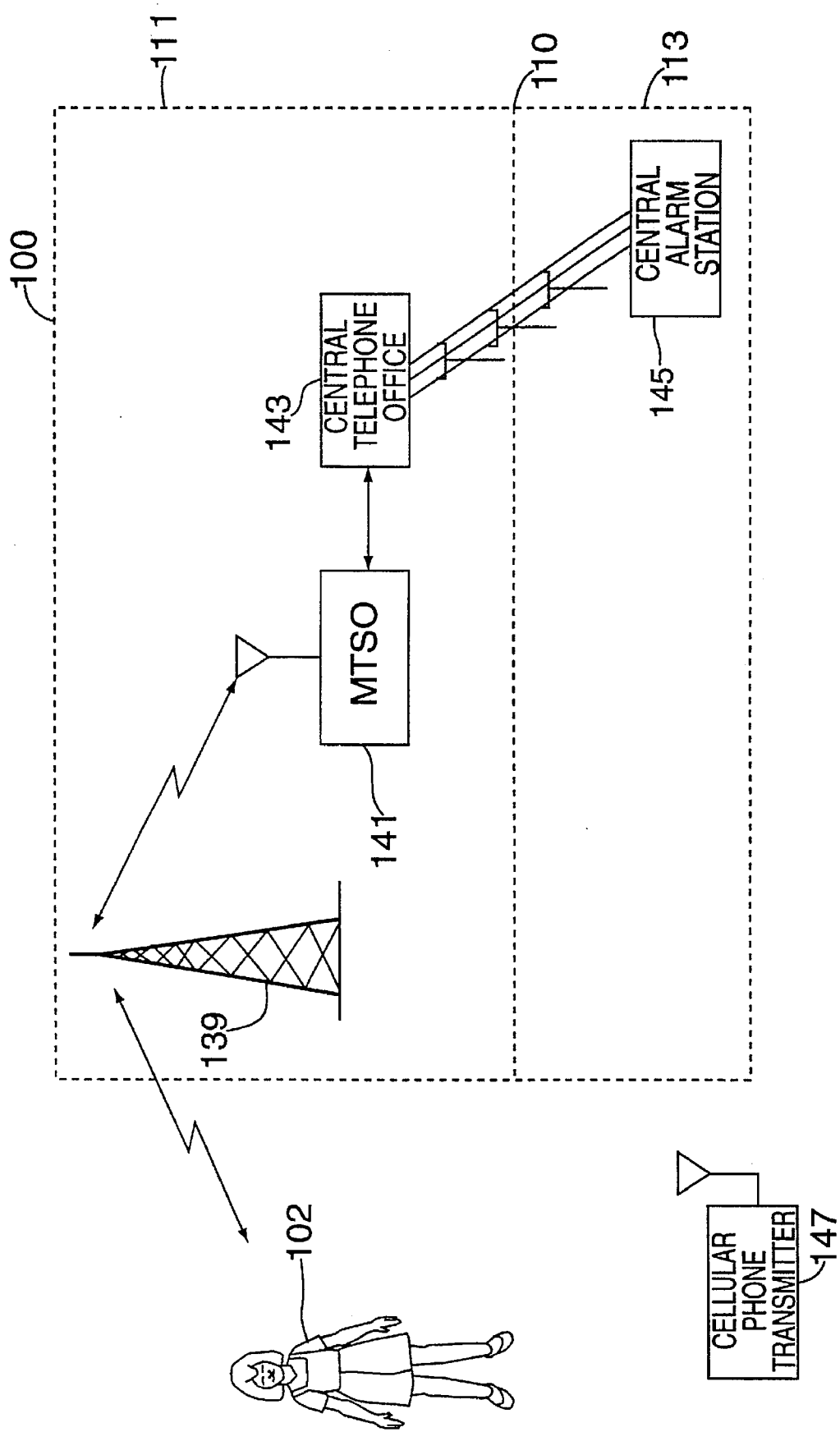

The cellular triangulation system for determining the location of an individual carrying an object is shown in FIGS. 2A and 2B and is generally referred to by reference numeral 100. In one or more embodiments, the alarm generating means 101 may be disposed within the housing of any one of the several embodiments of the objects. System 100 includes alarm generating means 101 coupled through a combination modem and dialer 103 to the input and output, respectively, of a transmitter means 105 and a triggering receiver means 107. Coupled to the input of the alarm generating means 101 are pressure sensitive means 109. Referring to FIG. 2B, the system 100 also comprises a remote activation means 110 which comprises a remote receiver means 111, which is coupled to a remote position locating means 113 and a cellular phone transmitter 147. Referring back to FIG. 2A, the pressure sensitive means 109 comprise an activate channel 115 and a deactivate channel 117. The activate channel 115 comprises first pressure sensitive element(s) 119 which are coupled to first conditioning means 121, the latter being connected to an input of the alarm generating means 101. The deactivate channel 117 comprises second pressure sensitive element (s) 123 coupled to second conditioning means 125, the latter also being connected to an input of the alarm generating means 101. In one embodiment, the alarm generating means 101 may include a central microprocessor and memory or microprocessor 127, which has coupled thereto a time/date generator 129, a phone number generator 131 and a identification code generator 133. Both the transmitter means or transmitter 105 and the triggering receiver means 107 are connected to an antenna switch 135, which is in turn connected to a cellular phone antenna 137. Referring back to FIG. 2B, the remote receiver means 111 comprises a fixed array of cellular sites 139 (only one of which is shown), each of which includes a wireless signal detecting and generating means and a controlling mobile telecommunication switching office ("MTSO") 141 coupled to a central telephone office 143. The remote positioning locating means 113 comprises a central alarm station 145 to which the output of the central telephone office 143 is coupled. The remote activation means 110 also includes a cellular phone transmitter 147.

In operation, when the pressure sensitive elements 119 of the housing of the object are actuated by the appropriate pressure, it results in the generation of an enabling triggering signal generated by the conditioning means 121, which signal is coupled to the central microprocessor and memory 127. The central microprocessor and memory component 127, which is activated by this triggering signal, continuously attempts to dial an emergency phone number stored in the permanent memory of the phone number generator 131 through the modem and dialer 103 in order to transmit a distress or alarm signal to the input of the transmitter means or cellular phone transmitter 105. The alarm signal contains a message which is digitally coded, which message includes the unique identification number stored in the identification code generator 133, the time and date of activation from the time and date generator 129, and the method of activation (remote or by the individual carrying the object). The modem and the dialer 103 generate dialing tones and convert the message of the alarm signal to telephone compatible tones which are coupled to the cellular phone transmitter 105 through the microprocessor 127, and then to the cellular phone antenna 137 through an antenna switch 135. Referring now to FIG. 2B, the alarm signal is received by a cellular telephone network, and more particularly its cellular phone antenna sites 139, which simultaneously receive the transmitted alarm signals. Such detected alarm signals are then transmitted to MTSO 141 which transmits them to the central alarm station 145 through the central telephone office 143. By utilizing a computer within the central alarm station 145, which processes the alarm signal messages, the approximate location of the individual carrying the object is determined by selecting a number of cell sites 139 which have the highest signal strength and by the use of an algorithm, together with a process of "articulation", all of which is discussed in detail in U.S. Pat. No. 4,891,650 issued to Sheffer.

The system 100 can also be activated remotely by an individual cellular phone transmitter 147 or by the central alarm station 145 through the cellular telephone network, which activation signal is detected by the cellular phone receiver 107, disposed within the object's housing. This receiver 107 couples an enabling or triggering signal to the alarm generating means 101 through the interconnecting modem and dialing component 103. More specifically, the triggering signal is coupled to the central microprocessor and memory 127, which as discussed previously, initiates a process wherein a distress or alarm signal is connected to the cellular phone transmitter 105, which transmits the alarm signal through its antenna 137 and hence to the cellular telephone network shown in FIG. 2B. The signal can be terminated through the deactivate channel 117 by application of appropriate pressure, resulting in the generating of a disabling or terminate signal applied to the microprocessor 127.

The preferred embodiment of the invention is the geoposition cellular system for determining the location of an individual and is shown in FIGS. 3A and 3B and is generally referred to by reference number 200. That portion of the system 200 shown in FIG. 3A is shown disposed within the housing of a key fob 20 (FIG. 1C). The system 200 comprises a remote position locating means 201, which transmits location signals in response to interrogation signals, an alarm generating means 203 for generating an alarm signal in response to a triggering signal, pressure sensitive means 205, coupled to the alarm generating means 203, for generating an enabling or triggering signal when activated, position generating means 207 coupled to the alarm generating means 203, for transmitting the interrogation signal and for detecting transmitted location signal from the position locating means 201, and transmitter means 209, coupled to the alarm generating means 203, for transmitting the alarm signals. The latter four components are disposed within the object, the key fob 20. The system 200 further comprises a cellular telephone network which includes a combination remote receiver means and activation means 211. The remote receiver means portion detects the alarm signals, including its location signal; the remote activation means portion transmits an activation signal. The system 200 also includes a triggering receiver means 213, disposed within the key fob 20, coupled to the alarm generating means 203, for detecting the activation signal and which in turn produces or generates an enabling or triggering signal.

The remote position locating means 201 comprises multiple satellites 215 in the existing global geoposition system; these satellites 215 transmit location signals in response to an interrogation signal. The alarm generating means 203, comprises a central microprocessor and memory or microprocessor 217, which has coupled thereto a time/date generator 219, a phone number generator 221 and an identification code generator 223. The position generating means 207, comprises a global position generator 225, coupled at one output to the central microprocessor 217 and at another output to a satellite antenna 227. The pressure sensitive means 205 comprise an activate channel 229 and a deactivate channel 230. The activate channel 229 comprises pressure sensitive element(s) 223 which are coupled to conditioning means 235, the latter being connected to an input of the microprocessor 217. The deactivate channel 230 comprises second pressure sensitive element(s) 237 coupled to second conditioning means 239, the latter also being connected to an input of the microprocessor 217. The transmitter means 209 comprises a combination modem and dialer 236, cellular phone transmitter and receiver, 210 and 213, respectively, antenna switch 231 and cellular antenna phone 234. Both the cellular phone transmitter 210 and the triggering receiver means 213, are connected to the antenna switch 231, which is in turn connected to the cellular phone antenna 234. The microprocessor 217 is coupled through a combination modem and dialer 236 to the input and output, respectively, of cellular phone transmitter 210 and cellular phone receiver 213. Referring to FIG. 3A, the cellular phone transmitter 210, transmits the alarm signal, including location signals, to a cellular telephone network having a MTSO 211 or combination remote receiver and activation means discussed previously.

In operation, when the pressure sensitive elements 233 on the housing of the key fob 20, are activated by the appropriate pressure, the generation of an enabling or triggering signal results through the conditioning means 235, which signal is coupled to the central microprocessor and memory component 217, which is activated by this triggering signal and continuously attempts to dial an emergency phone number stored in the permanent memory of the phone number generator 221 through the modem and dialer 236 in order to transmit a distress or alarm signal to the input of the cellular phone transmitter 210. The alarm signal contains a message which is digitally coded, which message includes the unique identification number stored in the identification code generator 223, the time and date of the activation from the time and date generator 219, the method of activation (remote or by the individual carrying the object) and location data or signals from the global position generator 225. More specifically the global position generator 225 is activated by the microprocessor 217 in response to a triggering signal and transmits an interrogation signal through satellite antenna 227. The satellites 215 then transmit location signals in response to said interrogation signal, which are detected by the antenna 227 of the global position generator 225, and which becomes part of the transmitted alarm signal. The modem and dialer 236 generate dialing tones and convert the message of the alarm signal to telephone compatible tones which are coupled to the cellular phone transmitter 210, and then to the cellular phone antenna 234 through an antenna switch 231. Referring to FIG. 3B, the alarm signal is received by a cellular telephone network, and more particularly to the combination remote receiver and activation means 211.

This system 200 can also be activated remotely by an individual cellular phone transmitter 127 (FIG. 2B), or by a combination remote activation means/remote receiver means 211, through a cellular telephone network, which activation signal is detected by a cellular phone receiver 213, disposed within the housing of the key fob 20. This receiver 213 couples an enabling or triggering signal to the alarm generating means 203 through the interconnecting modem and dialer component 236. More specifically, the triggering signal is coupled to the central microprocessor and memory 215, which as discussed previously, initiates a process wherein a distress or alarm signal is connected to the cellular phone transmitter 210, which transmits the alarm signal through its antenna 234 and then to the cellular telephone network. The alarm signal can be terminated through the deactivate channel 230 by application of appropriate pressure, resulting in the generation of a disabling or terminate signal to the microprocessor 217.

Figure 4A:
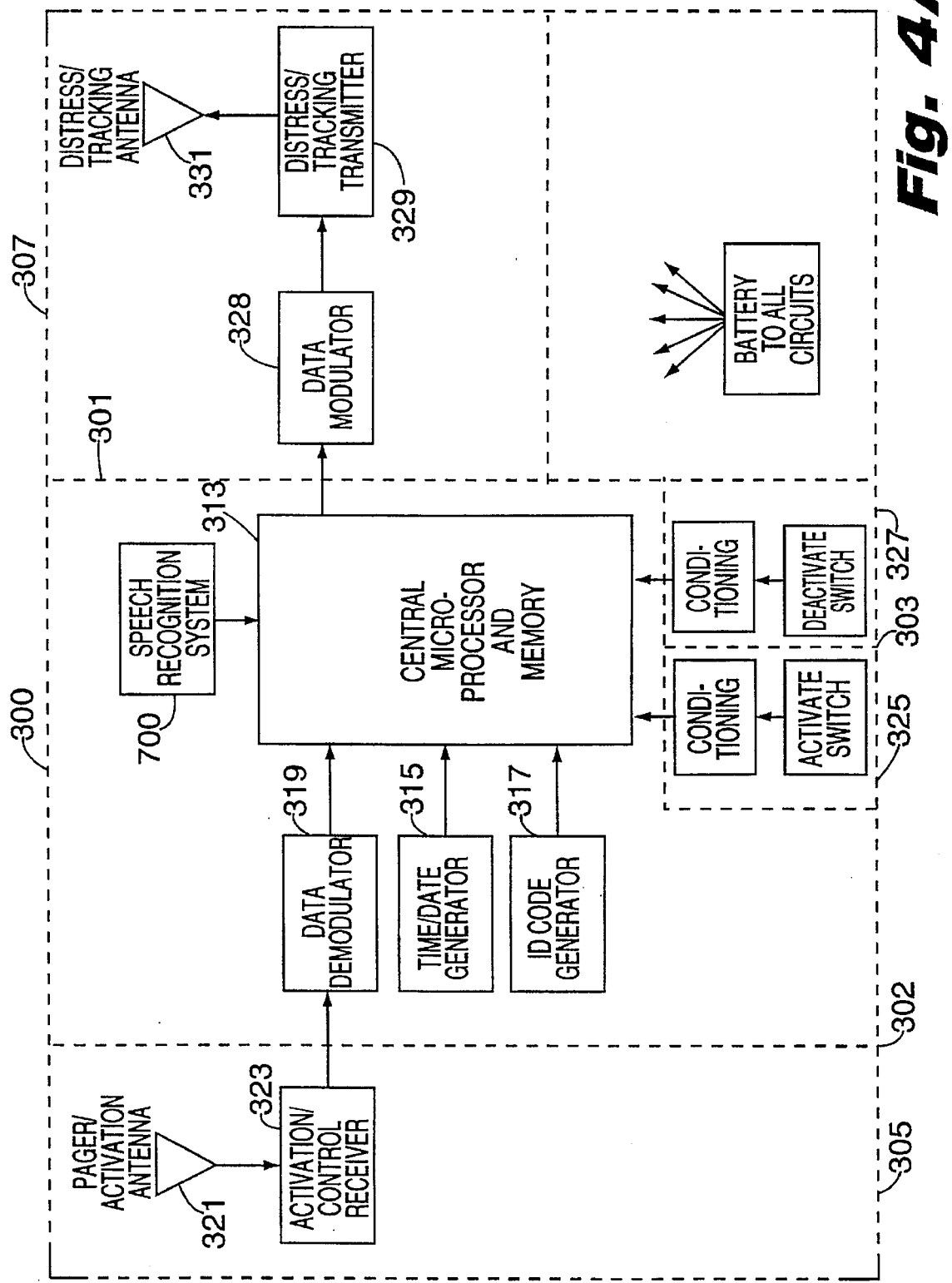
FIGS. 4A and 4B are simplified block diagrams of a mobile tracking system for determining the location of an individual.
Figure 4B:
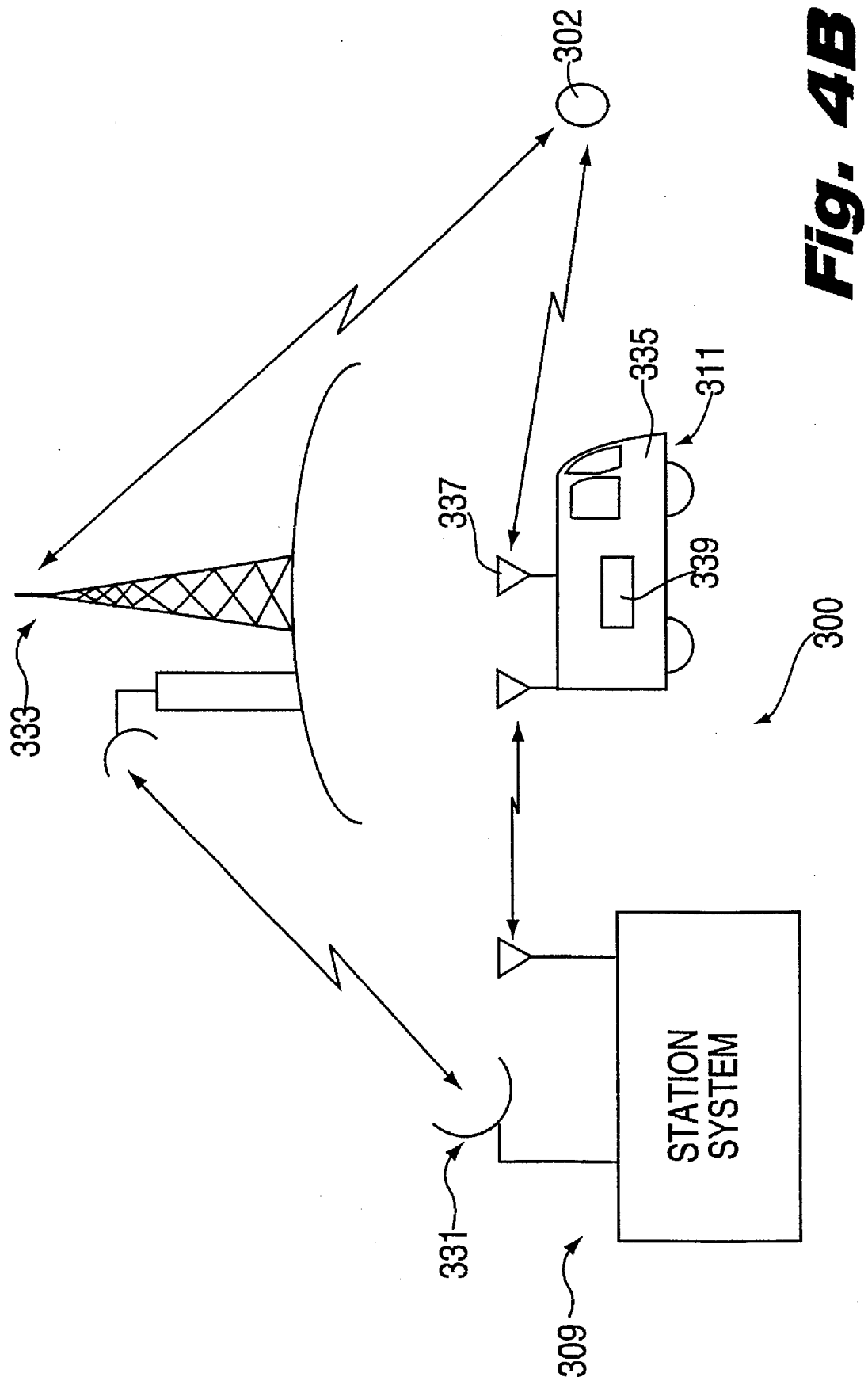
Figure 6:
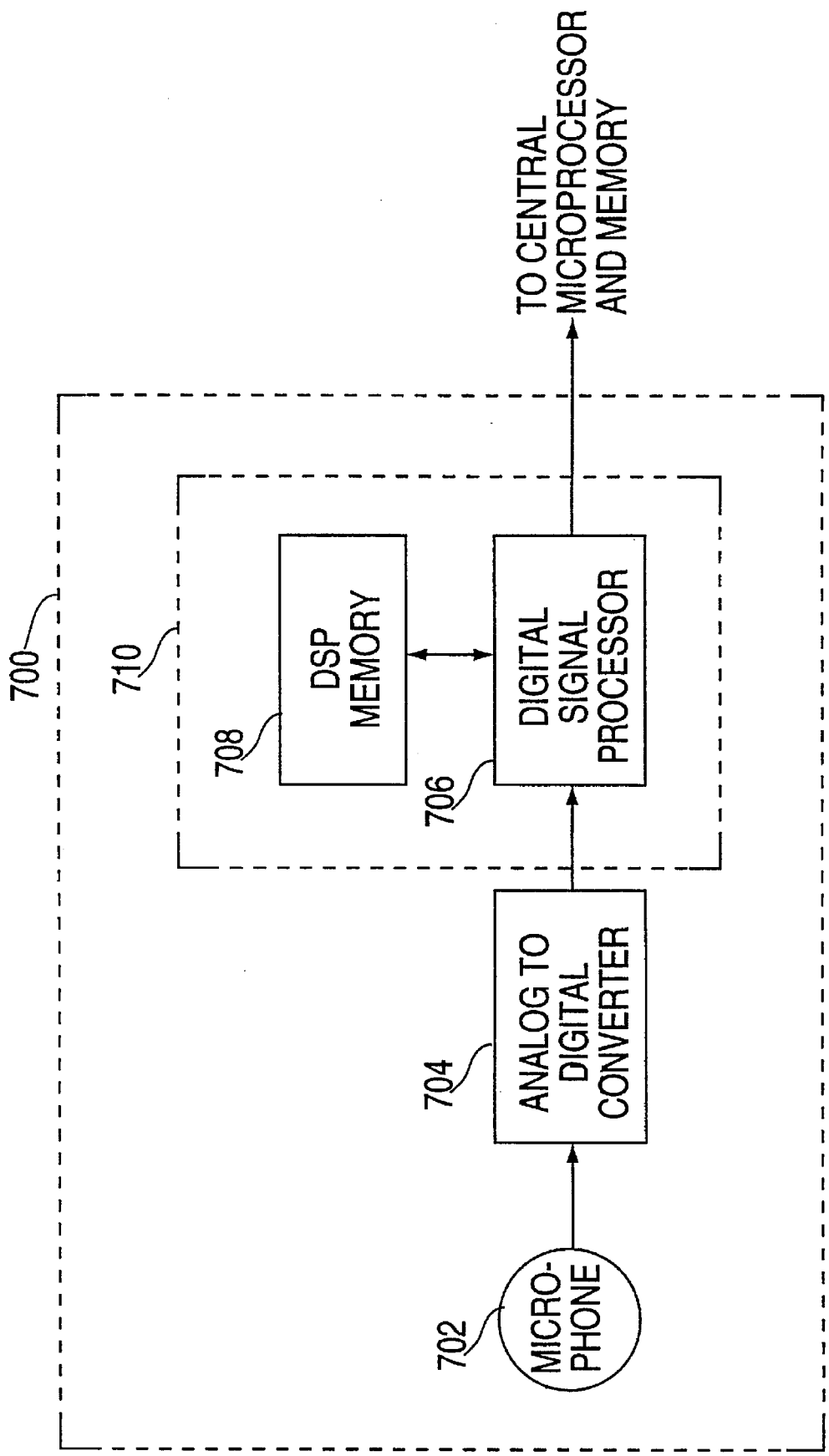
FIG. 6 is a block diagram of a speech recognition system of the present invention.

The mobile tracking system for determining the location of an individual is shown in FIGS. 4A and 4B and is generally referred to by reference numeral 300. That portion of the system 300 shown in FIG. 4A is disposed within the housing of an object 302. The system 300 comprises an alarm generating means 301 for generating an alarm signal in response to a triggering signal, pressure sensitive means 303, coupled to the alarm generating means 301, for generating an enabling or triggering signal when actuated, triggering receiver means 305 for receiving and detecting an activation signal and producing an enabling or triggering signal in response thereto, which triggering signal is coupled to said alarm generating means 301, and transmitter means 307, for transmitting the alarm signals. These four components are disposed within the object 301. The system 300 further comprises a remote activation means 309 (FIG. 4B) for transmitting an activation signal to the triggering receiver means 305 and a remote mobile direction-finding means 311, for detecting alarm signals from the transmitter 307 of the object 302 in response to an activation signal from the remote activation means 309. The direction-finding means 311 also transmits a command signal to the remote activation means 309 which in response thereto increases the rate of transmission of the activation signal, resulting in an increase in the rate of transmission of the alarm signal from the object 302.

The alarm generating means 301, comprises a central microprocessor and memory or microprocessor 313, which has coupled thereto a time/date generator 315, a phone number generator 317 and a data demodulator 319. The triggering receiver means 305 comprises a pager/activator antenna 321 which is connected to the input of an activation/control receiver 323 which has its output triggering signal coupled to the data demodulator 319 of the alarm generator means 301. The pressure sensitive means 303 comprise an activate channel 325 and a deactivate channel 327, which components are the same as the corresponding channels of the two previous described systems and therefore are not further described in detail. The transmitter means 307 comprises data modulator 328, which is coupled to the alarm generating means 301, a distress/tracking transmitter 329 and its output is connected to a distress/tracking antenna 331. Referring to FIG. 4B, when object 302 transmits an alarm signal, it is detected by the remote, mobile, direction finding means 311. This alarm signal can be initiated by the individual carrying the object 302 or by an activation signal transmitted by the remote activation means 309, through antenna 331 to stationary broadcast transmitters 333, which in turn broadcast the actuation signal, which is detected by the object 302. Mobile direction-finding means 311, in the form of a tracking vehicle 335, is equipped with a direction-finding antenna 337 and a tracking receiver and display 339, detect the alarm signal transmitted by the object 302. The direction-finding means 311 transmits a command signal to the remote activation means 309, which in response thereto, transmits an actuation signal through antenna 331, which increases the rate of transmission of the alarm signal.

In operation, when the pressure sensitive means 303 of the activation channel 325, are activated by the appropriate pressure, the generation of an enabling or triggering signal results, which signal is coupled to the microprocessor 313, which is activated by the triggering signal, periodically transmits a distress or alarm signal to the distress/tracking transmitter 307 through the intervening data modulator 328. The alarm signal contains a message which is digitally coded, which message includes the identification number stored in the identification code generator 317, the time and date of activation from the time and date generator 315 and the method of activation. This system 300 can also be actuated remotely by the remote activation means 309 or by a specialized transmitter or existing pager system (neither of which is shown) which transmits an activation signal which is detected by the activation/control receiver 323 disposed within the housing of the object 302. The receiver 323 couples a triggering signal to the alarm generating means 301, which alarm signal is processed as previously described, resulting in an alarm signal being transmitted from distress/tracking transmitter 307. The method of tracking and locating the object 302 depicted in FIG. 4B has already been generally described above, and a detailed description therefor is contained in U.S. Pat. No. 4,908,629 issued to Apsell, and is referred to as the Lo-Jack system, manufactured by the Lo-Jack Corporation, Boston, Mass.

In order to conceal the purpose of the object, the following described embodiments employ pressure sensitive elements or pressure transducer(s) in the form of gage elements. A strain gage is an instrumental device used to measure the dimensional change within or on the surface of a specimen. The electrical type strain gage may operate on the measurement of a capacitance, inductance or a resistance change that is proportional to strain. Such strain gage elements convert a small mechanical motion to an electrical signal by virtue of the fact that when a metal (wire or foil) or semiconductor is stretched, its resistance is increased. These pressure sensitive elements are concealed within or on the housing of the object, and the other components of the object, such as the alarm generating means, transmitters and receivers, are disposed within the housing. The pressure sensitive elements are disposed on or within the housing, such that when the housing is bent, twisted or pushed in a particular manner, a triggering signal is generated. In the following three figures on the strain gages are shown in solid lines even though they are disposed within the housing of the objects. Referring now to FIG. 5A, a key fob object 400 is depicted, comprising a flexible housing means or housing 401 having a longitudinal axis 402, and two strain gages 403 (G1) and 404 (G2) having longitudinal axes 405 and 406 respectively, mounted at right angles with respect to one another within the housing 401. A bending action at both ends 407, around transverse axis 409, of the housing 401, will equally elongate both strain gages 403 and 404 while a twisting action around the longitudinal axes 405 of strain gage 403 will elongate strain gage 404 without affecting the other gage 403. Referring now to FIG. 5B, another key fob object 500 is depicted. It comprises a flexible housing means or housing 501 having ends 502 and a longitudinal axis 511, and two strain gages 505 (G2) and 507 (G1) having longitudinal axes 509 and 511, respectively. A bending action (around axis 509) at both ends 502 of the housing 501 will elongate strain gage 507 without affecting the other gage 505. Referring now to FIG. 5C, a pendant object 700 is depicted. It comprises a flexible housing means or housing 701 and a single strain gage (G1). Pressing at or near the center area 705 of the housing 701 will elongate the strain gage 703. Referring now to FIG. 5D, this circuit 600 is designed to trigger only when the housing 401 of key fob object 400 is twisted and when the housing 501 of key fob 500 is bent. This circuit 600 comprises a regulated power supply 601 and pressure sensitive means 603, the latter comprising pressure sensitive elements 605 and conditioning means 607 having a triggering signal output 609. The regulated power supply 601 is applied across a bridge circuit 611 comprising strain gages G1 and G2 on one leg and fixed resistors R1 and R2 on the other leg. The output of bridge circuit 611 is applied to a differential amplifier 613. If strain gages G1 and G2 change resistance equally (such as when housing 401 is bent around transverse axis 409), there will be no change in the output of the bridge circuit 611. When however, the housing 401 is twisted as previously described, gage 404 (G2) will elongate while strain gage 403 (G1) remains unaffected; this action will produce a signal at the output of amplifier 613. The output is applied to a filter 615, which is used to reduce transients and noise and can be used to require that the bending or twisting action be maintained for a minimum predetermined period of time to produce a triggering output signal. The filter 615 output is applied to comparators 617 and 619 which compare the voltage generated by the bending or twisting action to a predetermined minimum threshold reference voltage generated by a reference voltage source 621. The predetermined minimum threshold reference voltage is calibrated to the desired power needed to produce a triggering output voltage. Each of the comparators 617 and 619 produce a digital output voltage signal in only one direction of twisting (FIG. 5A) or bending (FIG. 5B) of the housing when the strain gages are not equally elongated and their elongations are significantly different. The comparator outputs are then applied individually to the two inputs of an OR circuit 623, whose output 609 is the triggering output applied to the central microprocessor and memory. If only one direction of twisting or bending action is desired to cause triggering, then only one comparator is needed and the OR circuit is unnecessary.

In the embodiment of FIG. 5C, which utilized a single strain gage 703 (G1), the circuit 600 can be used except that the second strain gage element G2 would be replaced by a fixed resistor.

In a further embodiment similar to the preferred embodiment shown in FIGS. 7–11, wrist watch WW and belt pod unit BP may be provided in a single information receiving and transmitting unit.

It should be understood that this invention is not limited to the specific details of construction and arrangements herein illustrated and/or described, and that changes and modifications may occur to one skilled in the art without departing from the spirit and scope of the invention.

I claim:

1. Interactive individual location and monitoring system comprising:

a. a central monitoring system for maintaining health, location, and other data with respect to a plurality of clients, including said individual;

b. an information receiver and transmitting unit carried by said individual in a manner for conveniently receiving medical and other information selected by and inputted directly from said individual and broadcasting locally by radio said information in a region proximate to said individual;

c. pod means worn by said individual including transponder means for receiving said information from said information receiver and transmitting unit and transmitting said information to said central monitoring system, said pod means including means for tracking the location of said individual and transmitting said location to said central monitoring system;

d. said pod means including a triaxial accelerometer gathering acceleration data for transmission of said data to said central monitoring station for analysis at a later time;

e. said central monitoring system including means for broadcasting alerts and queries directed to said individual, said transponder pod means receiving and rebroadcasting said alerts and queries locally, said information receiver and transmitting unit including means to receive said alerts and queries, said information receiver and transmitting unit including vibratory annunciator means for alerting said individual to receipt of a signal from said pod means.

2. The interactive individual location and monitoring system of claim 1 in which said information receiver and transmitting unit has the appearance of a wrist watch worn by said individual in a manner to permit convenient access to input and receive information, and including only sufficient battery power to communicate by wireless means to said pod means.

3. The interactive individual location and monitoring system of claim 1 in which said pod means is secreted within the clothing of, or within a pack carried by, said individual and carrying sufficient battery power to provide long distance radio communications with said central monitoring station and obtain location information from satellites.

4. The interactive individual location and monitoring system of claim 3 in which all communications of said information and data between said central monitoring system and said pod means are encrypted.

5. The interactive individual location and monitoring system of claim 1 in which said central monitoring system includes means for tracking and displaying the movements of said individual.

6. The interactive individual location and monitoring system of claim 5 in which said information receiver and transmitting unit includes a plurality of color coded buttons for initiating transmittal of signals representing different types of emergencies including "accident", "medical", "hold-up", and "kidnapping".

7. The interactive individual location and monitoring system of claim 1 in which said pod means includes alarm button means for initiating an alarm signal to said central monitoring station.

8. The interactive individual location and monitoring system of claim 1 in which said information receiver and transmitting unit includes means for monitoring the pulse rate of said individual and initiating automatically the transmittal of a signal in the event a predetermined anomaly in the pulse rate occurs.

9. The interactive individual location and monitoring system as in claim 1 wherein said central monitoring system further includes a write only file storage means storing periodic data packets from each client of said plurality of clients, including said individual, said periodic data packets stored in said storage means, said periodic data packets intermittently read upon the occurrence of a predetermined selective event upon authorization from designated officials of said central monitoring system.

10. The interactive individual location and monitoring system as in claim 9 wherein said write only file storage means provides a time line of coherent data covering a long term period of time.

11. The interactive individual location and monitoring system as in claim 10 wherein said subsequent periodic packets of data overlay the oldest periodic packets of data of said periodic packets of data in said write only file storage means.

12. The interactive individual location and monitoring system as in claim 1 wherein said triaxial accelerometer provides said data to a neural network and a fuzzy logic processor in said central monitoring system to infer modes of transportation activity.

13. The interactive individual location and monitoring system as in claim 1 wherein said central monitoring system has a display means displaying said data, said data display means having a format thereof consisting of alphanumeric characters and/or graphical map data.

14. The interactive individual location and monitoring system as in claim 13 wherein said data display means is audio-enhanced.

15. The interactive individual location and monitoring system as in claim 13 wherein said graphical map data of said data display means is a multi-color graphical map display showing a global view of movement of the individual over an extended period of time.

16. A method of remotely and interactively communicating with and monitoring the location and condition of an individual comprising the steps of:

a. establishing a central monitoring system for maintaining health, location, and other data with respect to said individual, b. transmitting location and condition information from said individual to said central monitoring system by the steps of inputting information to an information receiver and transmitting unit worn by said individual, broadcasting locally by radio said information by said information receiver and transmitting unit to a pod means also worn by said individual, and rebroadcasting said information by said pod means to said central monitoring system; and c. broadcasting alerts and queries by said central monitoring system for receipt and rebroadcast by said pod means to said information receiver and transmitting unit, said information receiver and transmitting unit alerting said individual to the receipt of said alerts and queries;

d. providing at least one microprocessor in said information receiver and transmitting unit which supports a continuous polling sequence monitoring alarm conditions including code word decoding and pulse rate anomalies, and, e. providing at least one further microprocessor in said pod means which supports a further continuous polling sequence monitoring updates of:
  i) global positioning system (GPS) location information;
  ii) said alarm conditions received from said information receiver and transmitting unit;
  iii) compressed ambient noise data; and,
  iv) accelerometer data;
  said further continuous polling sequence also monitoring:
  v) said queries from said central monitoring system; and, f. accumulating said data for transmission and sending said data as a single multi-data packet to said central monitoring system.

17. Interactive individual location and monitoring system comprising:

a. a central monitoring system for maintaining health, location, and other data with respect to said individual;

b. an information receiver and transmitter unit carried by said individual in a manner for conveniently receiving medical and other information selected by and inputted directly from said individual and broadcasting locally by radio said information in a region proximate to said individual; said information receiver and transmitter unit further communicating with c. a pod means including transponder means for transmitting said information to said central monitoring system, said pod means including means for tracking the location of said individual and transmitting said location to said central monitoring system;

d. said pod means including a triaxial accelerometer gathering acceleration data for transmission of said data to said central monitoring station for analysis at a later time;

e. said central monitoring system including means for broadcasting alerts and queries directed to said individual, said transponder pod means receiving and rebroadcasting said alerts and queries locally, said information receiver and transmitting unit including means to receive said alerts and queries, said information receiver and transmitting unit including vibratory annunciator means for alerting said individual to receipt of a signal from said pod means, said information receiver and transmitting unit having the appearance of a wrist watch worn by said individual in a manner to permit convenient access to input and receive information, and including only sufficient battery power to communicate by wireless means to said pod means, said pod means being secreted within the clothing of or packs carried by said individual and carrying sufficient battery power to provide long distance radio communications with said central monitoring station and obtain location information from satellites, wherein all communications between said central monitoring system and said pod means are encrypted, said central monitoring system including means for tracking and displaying the movements of said individual, said information receiver and transmitting unit including a plurality of color coded buttons for initiating transmittal of signals representing different types of emergencies including "accident", "medical", "hold-up", and "kidnapping", said pod means including an alarm button means for initiating an alarm signal to said central monitoring station, said information receiver and transmitter unit includes a means for monitoring the pulse rate of said individual and initiating automatically the transmittal of a signal in the event a predetermined anomaly in the pulse rate occurs, said central monitoring system further including a write only file storage means storing periodic data packets from each client, said periodic data packets stored in said storage means, said periodic data packets intermittently read upon the occurrence of a predetermined selective event upon authorization from designated officials of said central monitoring system, said write only file storage means providing a time line of coherent data covering a long term period, said subsequent periodic packets of data overlay the oldest periodic packets of data in said write only file storage means, said triaxial accelerometer provides said data to a neural network and fuzzy logic processor to infer modes of transportation activity, said central monitoring system having a display means displaying said data, said data display format consisting of alphanumeric characters and/or graphical map format, and, said graphical map data being a multi-color graphical map display showing a global view of movement of the individual over an extended period of time.

18. A system for determining the location of an individual comprising:

a) an object carried by said individual from which an alarm signal is generated, said object comprising:
   i) a housing means,
   ii) alarm generating means, disposed within said housing means, for generating an alarm signal, in response to a triggering signal,
   iii) means disposed on or within said housing means, coupled to said alarm generating means, for generating a triggering signal when actuated by pressure exerted against said means by said individual,
   iv) transmitter means, disposed within said housing means, coupling to said alarm generating means, for transmitting said alarm signal; and,
   v) said transmitter means including a triaxial accelerometer gathering acceleration data for transmission of said data to a central monitoring system;

b) remote receiver means, for detecting said alarm signal and producing an output signal in response thereto; and c) remote position locating means, coupled to said remote receiver means, for determining the location of said object in response to said output signal.

19. The system as recited in claim 18 wherein said system further comprises:

d) remote activation means, for transmitting an activation signal, and wherein said object further comprises,
   v) triggering receiver means, disposed within said housing means, coupled to said alarm generating means, for detecting said activation signal and producing a triggering signal in response thereto.

* * * * *